(12) United States Patent
Maekawa

(10) Patent No.: US 12,144,883 B2
(45) Date of Patent: *Nov. 19, 2024

(54) COSMETIC COMPOSITION

(71) Applicant: KAO CORPORATION, Tokyo (JP)

(72) Inventor: Tomoka Maekawa, Sumida-ku (JP)

(73) Assignee: KAO CORPORATION, Tokyo (JP)

( * ) Notice: Subject to any disclaimer, the term of this patent is extended or adjusted under 35 U.S.C. 154(b) by 68 days.

This patent is subject to a terminal disclaimer.

(21) Appl. No.: 17/999,874

(22) PCT Filed: May 27, 2021

(86) PCT No.: PCT/JP2021/020141
§ 371 (c)(1),
(2) Date: Nov. 25, 2022

(87) PCT Pub. No.: WO2021/246274
PCT Pub. Date: Dec. 9, 2021

(65) Prior Publication Data
US 2023/0240969 A1  Aug. 3, 2023

(30) Foreign Application Priority Data
Jun. 1, 2020  (JP) ................. 2020-095670

(51) Int. Cl.
*A61Q 5/10* (2006.01)
*A61K 8/891* (2006.01)
*A61K 8/898* (2006.01)
*A61Q 5/06* (2006.01)

(52) U.S. Cl.
CPC .............. *A61K 8/891* (2013.01); *A61K 8/898* (2013.01); *A61Q 5/065* (2013.01); *A61K 2800/10* (2013.01); *A61K 2800/43* (2013.01); *A61K 2800/60* (2013.01)

(58) Field of Classification Search
CPC .... A61K 8/891; A61K 8/898; A61K 2800/10; A61K 2800/43; A61K 2800/60; A61K 8/31; A61K 8/585; A61Q 5/065; A61Q 5/12
USPC .......................................................... 8/405
See application file for complete search history.

(56) References Cited

U.S. PATENT DOCUMENTS

| | | | | |
|---|---|---|---|---|
| 2004/0170586 A1* | 9/2004 | Ferrari | ................... | A61Q 19/00 424/63 |
| 2008/0127429 A1* | 6/2008 | Brun | ..................... | A61K 8/31 8/647 |
| 2010/0083446 A1* | 4/2010 | Brun | ..................... | A61K 8/891 8/405 |
| 2015/0139931 A1* | 5/2015 | Maekawa | ................ | A61Q 5/12 424/70.122 |
| 2015/0297498 A1* | 10/2015 | Ohba | .................... | A61K 8/895 525/474 |

FOREIGN PATENT DOCUMENTS

| | | |
|---|---|---|
| EP | 0 285 364 A1 | 10/1988 |
| EP | 2 135 596 A1 | 12/2009 |
| FR | 2 958 544 A1 | 10/2011 |
| JP | 63-79580 A | 4/1988 |
| JP | 4-45155 A | 2/1992 |
| JP | 10-265354 A | 10/1998 |
| JP | 2007-223930 A | 9/2007 |
| JP | 2012-197265 A | 10/2012 |
| JP | 2013-184897 | 9/2013 |
| JP | 2013-209323 A | 10/2013 |
| JP | 2015-515981 A | 6/2015 |
| JP | 2016-503433 A | 2/2016 |

OTHER PUBLICATIONS

STIC Search Report dated Mar. 27, 2024.*
International Search Report mailed on Aug. 3, 2021 in PCT/JP2021/020141 filed on May 27, 2021 (2 pages).
Extended European Search Report issued on Jun. 5, 2024 in corresponding European Patent Application No. 21818500.7, 9 pages.

* cited by examiner

*Primary Examiner* — Eisa B Elhilo
(74) *Attorney, Agent, or Firm* — Oblon, McClelland, Maier & Neustadt, L.L.P.

(57) ABSTRACT

A cosmetic composition including: (A) a silicone film-forming agent, and (B) a high-molecular-weight organopolysiloxane having a degree of polymerization of 2,600 or more and 4,500 or less. A ratio by mass of a content of the component (A) to a total content of the component (A) and the component (B), [(A)/((A)+(B))] is 50% or more and 98% or less, and a water content is 10% by mass or less.

13 Claims, No Drawings

COSMETIC COMPOSITION

CROSS REFERENCE TO RELATED APPLICATIONS

This application is a National Stage entry under 35 U.S.C. § 371 of PCT/JP2021/020141, filed on May 27, 2021, and claims priority to Japanese Patent Application No. 2020-095670, filed on Jun. 1, 2020. The entire contents of both are incorporated herein by reference.

FIELD OF THE INVENTION

The present invention relates to a cosmetic composition.

BACKGROUND OF THE INVENTION

It is known that hair is damaged and difficult to handle by external factors in daily life, and chemical treatment such as perm and color. In order to solve such a situation, a conditioning agent or a styling agent is used to impart gloss or smoothness to hair. However, many of these effects are lost by one shampooing, and products capable of sustaining the effects are desired.

Recently, in the field of cosmetics, a technique of forming a hydrophobic film has been investigated as a method of imparting a gloss and a smooth feel onto skin or hair.

For example, Patent Literature 1 (JP 2015-515981 T) discloses that a composition containing a continuous aqueous phase, and a discontinuous phase that contains a plasticized MQ-type silicone resin and/or a derivative thereof, and/or a plasticized MT-type silicone resin and/or a derivative thereof, in which the discontinuous phase is emulsified in the aqueous phase, is useful as a haircare product for treating split ends.

Patent Literature 2 (JP 2016-503433 T) discloses a composition containing a silicone resin and a silicone rubber, in which a mixture of the silicone resin and the silicone rubber have a softening point higher than 50° C. and an elastic modulus of 106 Pa or less at an environmental temperature, and discloses that when a formulation containing the composition is applied to hair, it can impart a smooth feel and a strong gloss to the hair.

As one hair dyeing technique, there is known a temporary hair dye technique of using a pigment as a colorant and forming a film that contains the colorant on hair for dyeing the hair. For example, Patent Literature 3 (JP H10-265354 A) discloses that a hair dye containing a volatile oil, a water-repellent polymer dissolving in the volatile oil, a powder, and a nonvolatile oil compatible with the volatile oil, in which at least a part of the powder is a color pigment, is applicable in a simple manner and secures good color duration not causing secondary adhesion after application.

SUMMARY OF THE INVENTION

The present invention relates to the following [1] to [7].

[1] A cosmetic composition containing (A) a silicone film-forming agent, and (B) a high-molecular-weight organopolysiloxane having a degree of polymerization of 2,600 or more and 4,500 or less, wherein a ratio by mass of the content of the component (A) to the total content of the component (A) and the component (B), [(A)/((A)+(B))] is 50% or more and 98% or less, and the water content is 10% by mass or less.

[2] The cosmetic composition according to the above [1], which is a hair cosmetic composition.

[3] The cosmetic composition according to the above [1], which is a hair dye composition.

[4] A method for treating a keratin substance, including a step of applying the cosmetic composition of the above [1] to a keratin substance and then drying it.

[5] A method for treating hair, including a step of applying the hair cosmetic composition of the above [2] to hair and then drying it.

[6] A method for dyeing hair, including a step of applying the hair dye composition of the above [3] to hair and then drying it.

[7] A cosmetic kit provided with the following compositions (I) and (II),
(I) a composition containing (A) a silicone film-forming agent,
(II) a composition containing (B) a high-molecular-weight organopolysiloxane having a degree of polymerization of 2,600 or more and 4,500 or less.

DETAILED DESCRIPTION OF THE INVENTION

Definition

"Polymer" used in the present specification means a compound corresponding to a repetition of one or plural units (these units are derived from a compound known as a monomer). This or these units are repeated at least two times preferably at least three times.

"Hair" used in the present specification means mainly head hair.

"Hydrophobic" used in the present specification means that a solubility in water of a substance is less than 1% by mass at 25° C.

"Film formation" used in the present specification means that, when applied to a substrate, a film is left thereon.

"Volatile" used in the present specification means a substance having a boiling point of 260° C. or lower under normal pressure.

[Cosmetic Composition]

The cosmetic composition of the present invention contains:
(A) a silicone film-forming agent, and
(B) a high-molecular-weight organopolysiloxane having a degree of polymerization of 2,600 or more and 4,500 or less, wherein:
a ratio by mass of the content of the component (A) to the total content of the component (A) and the component (B), [(A)/((A)+(B))] is 50% or more and 98% or less, and the water content is 10% by mass or less.

Having the above constitution, the cosmetic composition of the present invention can provide a dirt adhesion-preventing effect, a good feel and a high drying speed, and is, even after washing, excellent in the sustainability of these effects. In addition, when the cosmetic composition is used as a hair dye composition, it can impart the above effects to hair and secures good color duration with little discoloration by shampooing.

Washing and drying hair requires time and labor, and it is desired that the hair after conditioning treatment or hair dyeing treatment hardly becomes dirty and the drying speed after shampooing is rapid. However, Patent Literatures 1 to 3 refer to nothing relating these problems.

An object of the present invention is to provide a cosmetic composition which, when applied to keratin substances such as skin or hair, can impart thereto a dirt adhesion preventing effect, a good feel and a high drying speed, and is, even after washing, excellent in the sustainability of these effects.

The present inventor has found that a cosmetic composition containing a silicone film-forming agent and a high-molecular-weight organopolysiloxane having specific viscosity in a specific ratio by mass, and having a water content in a specific amount or less can solve the above-mentioned problems, and has completed the present invention.

According to the present invention, there can be provided a cosmetic composition which, when applied to keratin substances such as skin or hair, can impart thereto a dirt adhesion preventing effect, a good feel and a high drying speed, and is, even after washing, excellent in the sustainability of these effects. In addition, when the cosmetic composition is used as a hair dye composition, it can impart the above effects to hair and secures good color duration with little discoloration by shampooing.

The reason why the cosmetic composition of the present invention exhibits the above-mentioned effect is, though not clear, presumed as follows.

The cosmetic composition containing the component (A) and the component (B) is, when applied to the surface of a keratin substance, able to form a hydrophobic film.

The component (B) is considered to exhibit an effect of imparting a good feel to the surface of a keratin substance and an effect of imparting a dirt adhesion preventing effect thereto, and further to play a role of a surface protective function. In addition, since the component (B) has a viscosity falling within a specific range, it is considered that the composition can suppress stickiness and can give a good feel.

On the other hand, the component (A) is a hydrophobic film-forming agent, and is considered to sustain strength and durability of the entire formed film and also to exhibit a durability improving effect for various properties given to keratin substances owing to the synergistic effect with the component (B).

In the case where a functional powder to be mentioned below is blended in the cosmetic composition, the functional powder can be held in the film to enhance various functions and sustainability thereof.

It is considered that the water content in the cosmetic composition is defined to be 10% by mass or less, whereby the mixability of the component (A) and the component (B) is enhanced to form a uniform film on the surface of a keratin substance, and further a ratio by mass of the content of the component (A) to the total content of the component (A) and the component (B) having the above-mentioned effects is defined to fall within a specific range, whereby the composition can impart a dirt adhesion preventing effect while maintaining a good feel and a high drying speed.

Consequently, for example, in the case where the cosmetic composition is a hair cosmetic composition, it is considered that, when applied to hair, the composition imparts thereto a dirt adhesion preventing effect, a good feel and a high drying speed, and even after shampooing, these effects can be sustained. In addition, it is also considered that, in the case where the cosmetic composition is a hair dye composition such as a temporary hair dye composition or a semi-permanent hair dye composition, the composition can impart the above-mentioned effects to hair and can improve color duration with little discoloration by shampooing owing to the synergistic effect of the component (A) and the component (B).

The mechanism of the action of the present invention is not limited to the above.

Components contained in the cosmetic composition of the present invention are described below.

<Component (A): Silicone Film-Forming Agent>

The cosmetic composition of the present invention contains a silicone film-forming agent as the component (A). Containing the component (A), the cosmetic composition of the present invention is, when applied to a keratin substance such as skin or hair, able to form a hydrophobic film having high durability. In the case where a functional powder to be mentioned hereinunder is blended in the cosmetic composition, the functional powder can be held in the film to improve various functions and sustainability thereof.

As the component (A), a silicone film-forming agent usable in ordinary cosmetic materials can be used, and is preferably solid at 25° C.

From the viewpoint of improving film formability and durability, the component (A) is preferably at least one selected from the group consisting of the following components (A1) and (A2).

(A1) A silicone resin represented by an average formula, $(R^1)_m SiO_{(4-m)/2}$
wherein $R^1$ represents a hydrocarbon group having 1 or more and 12 or less carbon atoms and optionally substituted with fluorine, or a hydroxy group, plural $R^1$'s can be the same as or different from each other, and m is an average number, representing a number of more than 0 and less than 3,
which contains at least one unit selected from the group consisting of a T unit represented by $R^1 SiO_{3/2}$ and a Q unit represented by $SiO_{4/2}$.

(A2) A silicone polymer containing a polysiloxane moiety and a moiety formed of a non-silicone organic chain.

Preferably, the component (A1) includes those containing at least one selected from the group consisting of the following component (A1-1) and component (A1-2).

(A1-1) A silicone resin represented by the above-mentioned average formula, containing a T unit represented by $R^1 SiO_{3/2}$ and substantially not containing a Q unit represented by $SiO_{4/2}$.

(A1-2) A silicone resin represented by the above-mentioned average formula, and containing a Q unit represented by $SiO_{4/2}$ and an M unit represented by $(R^1)_3 SiO_{1/2}$.

Preferably, the component (A2) includes those containing at least one selected from the group consisting of the following component (A2-1) to (A2-4).

(A2-1) An acryl silicone polymer.
(A2-2) A silicone-modified alicyclic structure-containing polymer.
(A2-3) A silicone-modified pullulan.
(A2-4) A polyurea/urethane silicone.

(Component (A1))

The component (A1) is a silicone resin represented by an average formula, $(R^1)_m SiO_{(4-m)/2}$
wherein $R^1$ represents a hydrocarbon group having 1 or more and 12 or less carbon atoms and optionally substituted with fluorine, or a hydroxy group, plural $R^1$'s can be the same as or different from each other, and m is an average number, representing a number of more than 0 and less than 3,
which contains at least one unit selected from the group consisting of a T unit represented by $R^1 SiO_{3/2}$ and a Q unit represented by $SiO_{4/2}$.

The component (A1) is represented by the above-mentioned average formula and contains at least one unit selected from the above-mentioned T unit and Q unit, and therefore has a crosslinked structure in the molecule. Having the structure, the silicone resin is considered to be able to form a film having higher durability. The component (A1) does not contain a polyorganosiloxane cured product powder which is infusible and does not have a softening point and which is generally insoluble in an organic solvent.

In the average formula, $R^1$ represents a hydrocarbon group having 1 or more and 12 or less carbon atoms and optionally substituted with fluorine, or a hydroxy group. The carbon number of the hydrocarbon group is, from the viewpoint of improving film formability and durability, 1 or more and preferably 9 or less, more preferably 6 or less, even more preferably 4 or less.

The hydrocarbon group may be any of an aliphatic group or an aromatic group, and examples thereof include an alkyl group, an alkenyl group, an aryl group and an aralkyl group. The alkyl group and the alkenyl group may be linear or branched.

Among the above, from the viewpoint of availability and stability, the hydrocarbon group is preferably an alkyl group, an aryl group or an aralkyl group.

The alkyl group includes a methyl group, an ethyl group, an n-propyl group, an isopropyl group, various butyl groups, various pentyl groups, various hexyl groups, various heptyl groups, various octyl groups, various nonyl group, various decyl groups, various undecyl groups, and various dodecyl groups. The word "various" means a linear or branched hydrocarbon group, and for example, "various butyl groups" include "an n-butyl group, a sec-butyl group, an isobutyl group and a tert-butyl group".

The aryl group includes a phenyl group, a toluyl group, a dimethylphenyl group, and a naphthyl group, and is preferably a phenyl group.

The aralkyl group includes a benzyl group, a phenylethyl group, a phenylpropyl group, and a phenylbutyl group, and is preferably a phenylpropyl group.

In the case where $R^1$ is substituted with fluorine, at least one hydrogen atom of the hydrocarbon group may be substituted with a fluorine atom.

$R^1$ is, from the viewpoint of improving film formability and durability, preferably an optionally fluorine-substituted, alkyl group having 1 or more and 12 or less carbon atoms, aryl group having 6 or more and 12 or less carbon atoms or aralkyl group having 7 or more and 12 or less carbon atoms, more preferably an optionally fluorine-substituted, alkyl group having 1 or more and 8 or less carbon atoms or phenyl group, even more preferably an optionally fluorine-substituted, alkyl group having 1 or more and 6 or less carbon atoms or phenyl group. The fluorine-substituted alkyl group is preferably a group represented by $CF_3$—R— wherein R represents an alkylene group having 2 or more and 7 or less carbon atoms, preferably 2 or more and 5 or less carbon atoms.

$R^1$ is more preferably a trifluoropropyl group, an alkyl group having 1 or more and 4 or less carbon atoms, or a phenyl group, even more preferably a trifluoropropyl group, a methyl group, an ethyl group, an n-propyl group, an isopropyl group or an n-butyl group, further more preferably a trifluoropropyl group, a methyl group or an n-propyl group, and further more preferably a methyl group.

The component (A1) may contain at least one unit selected from the group consisting of a T unit represented by $R^1SiO_{3/2}$ and a Q unit represented by $SiO_{4/2}$ and is, from the viewpoint of improving film formability and durability, preferably further contains at least one unit selected from the group consisting of an M unit represented by $(R^1)_3SiO_{1/2}$ and a D unit represented by $(R^1)_2SiO_{2/2}$. $R^1$ is the same as above.

From the viewpoint of improving film formability and durability, the component (A1) is preferably at least one selected from the group consisting of a silicone resin (A1-1) represented by the above-mentioned average formula, containing a T unit represented by $R^1SiO_{3/2}$ and substantially not containing a Q unit represented by $SiO_{4/2}$, and a silicone resin (A1-2) represented by the above-mentioned average formula, and containing a Q unit represented by $SiO_{4/2}$ and an M unit represented by $(R^1)_3SiO_{1/2}$.

[Silicone Resin (A1-1)]

The silicone resin (A1-1) represented by the above-mentioned average formula, containing a T unit represented by $R^1SiO_{3/2}$ and substantially not containing a Q unit represented by $SiO_{4/2}$ (hereinafter also referred to as "component (A1-1)") is a silicone resin containing a T unit and may contain an M unit and a D unit, and is preferably a silicone resin containing a T unit and optionally containing an M unit, which is represented by $[R^1SiO_{3/2}]_a[(R^1)_3SiO_{1/2}]_b$ wherein a and b each are an average repeating unit number, and a>0 and b≥0. The wording "substantially not containing XX" means the constituent ratio of XX in the silicone resin is less than 1 mol %.

$R^1$ is the same as above, and is preferably an alkyl group having 1 or more and 4 or less carbon atoms or a phenyl group, more preferably a methyl group, an ethyl group, an n-propyl group or an isopropyl group, even more preferably a methyl group, an n-propyl group or an isopropyl group.

The component (A1-1) includes polysilsesquioxanes such as polymethylsilsesquioxane, polypropylsilsesquioxane, polyphenylsilsesquioxane, polymethylphenylsilsesquioxane, and fluorine-modified alkyldimethylpolysilsesquioxanes, and among these, one or more can be used. Fluorine-modified alkyldimethylpolysilsesquioxanes include, as INCI nomenclature, trifluoropropyldimethylsiloxy/trimethylsiloxy)silsesquioxane.

Above all, from the viewpoint of improving film formability and durability, the component (A1-1) is preferably at least one selected from the group consisting of polymethylsilsesquioxane and polypropylsilsesquioxane.

Commercial products of the component (A1-1) include SilForm Flexible Resin (polymethylsilsesquioxane), SilForm FR-5 (polydimethylsiloxane solution of (trifluoropropyldimethylsiloxy/trimethylsiloxy)silsesquioxane) (all by Momentive Performance Materials Corporation), DOWSIL 680 ID Fluid (isododecane solution of 75 mass % polypropylsilsesquioxane) (by Day Toray Corporation), SR-21 (polyphenylsilsesquioxane), SR-23 (polyphenylsilsesquioxane), SR-33 (polymethylphenylsilsesquioxane) (all by Konishi Chemical Industry Co., Ltd.).

[Silicone Resin (A1-2)]

The silicone resin (A1-2) represented by the above-mentioned average formula, and containing a Q unit represented by $SiO_{4/2}$ and an M unit represented by $(R^1)_3SiO_{1/2}$ (hereinafter also referred to as "component (A1-2)" is a silicone resin substantially containing a Q unit and an M unit and optionally containing a D unit or a T unit, and is preferably a silicone resin represented by $[SiO_{4/2}]_c[(R^1)_3SiO_{1/2}]_d$ wherein c and d each are an average repeating unit number and c>0 and d>0.

$R^1$ is the same as above, and is preferably an optionally-fluorine substituted, alkyl group having 1 or more and 6 or less carbon atoms or phenyl group, more preferably a trifluoropropyl group, an alkyl group having 1 or more and 4 or less carbon atoms, or a phenyl group, even more preferably a trifluropropyl group, methyl group, an ethyl group, an n-propyl group, or an isopropyl group, further more preferably a trifluoropropyl group or a methyl group, and further more preferably a methyl group.

The component (A1-2) includes trimethylsiloxysilicate, phenylpropyldimethylsiloxysilicate, fluorine-modified alkyldimethylsiloxysilicates, and crosspolymers produced by crosslinking these siloxysilicates with dimethiconol, and at least one of these can be used. Fluorine-modified alkyldimethylsiloxysilicates include trifluoroalkyldimethyltrimethylsiloxysilicate, such as trifluoropropyldimethyltrimethylsiloxysilicate of, as ICNI nomenclature, trifluoropropyldimethyl/trimethylsiloxysilicate. Crosspolymers produced by crosslinking siloxysilicates with dimethiconol include, as ICNI nomenclature, (trimethylsiloxysilicate/dimethiconol) crosspolymer.

Above all, from the viewpoint of improving film formability and durability, the component (A1-2) is preferably at least one selected from the group consisting of trimethylsiloxysilicate, trifluoropropyldimethyltrimethylsiloxysilicate and (trimethylsiloxysilicate/dimethiconol) crosspolymer, more preferably at least one selected from the group consisting of trimethylsiloxysilicate, and trifluoropropyldimethyltrimethylsiloxysilicate, even more preferably trimethylsiloxysilicate.

Commercial products of trimethylsiloxysilicate of the component (A1-2) include KF-7312J (50 mass % decamethylcyclopentasiloxane solution), KF-9021 (50 mass % decamethylcyclopentasiloxane solution), X-21-5249 (50 mass % decamethylcyclopentasiloxane solution), X-21-5595 (60 mass % isododecane solution), and X-21-5616 (60 mass % isododecane solution) (all by Shin-Etsu Chemical Industry Co., Ltd.), SS4267 (35 mass % dimethylpolysiloxane solution), SR1000, SS4230 (45 mass % cyclopentasiloxane solution), SS4267 (35 mass % dimethylpolysiloxane solution), and Silsoft 74 (75 mass % isododecane solution) (all by Momentive Performance Materials Corporation), BY11-018 (30 mass % cyclopentasiloxane solution), and MQ-1600 Solid Resin (all by Dow Toray Corporation), and BELSIL TMS 803 (by Wacker Asahi Kasei Silicone Co., Ltd.).

Commercial products of phenylpropyldimethylsiloxysilicate include SilShine 151 (by Momentive Performance Materials Corporation).

Commercial products of fluorine-modified alkyldimethylsiloxysilicates include, XS66-B8226 (50 mass % cyclopentasiloxane solution), XS66-C1191, and XS66-B8636 (50 mass % dimethicone solution) (all by Momentive Performance Materials Corporation), as INCI nomenclature, (trifluoropropyldimethyl/trimethylsiloxysilicate).

Commercial products of trimethylsiloxysilicate crosspolymer include DOWSIL FC-5002 IDD Resin Gum (40 mass % isododecane solution of (trimethylsiloxysilicate/dimethiconol) crosspolymer) (by Dow Toray Corporation).
(Component (A2))

The component (A2) is a silicone polymer containing a polysiloxane moiety and a moiety formed of a non-silicone organic chain. The non-organic silicone organic monomer to constitute the moiety of a non-silicone organic chain is, from the viewpoint of availability on the market, preferably selectable from a radical-polymerizable ethylenically-unsaturated monomer, a polycondensation-polymerizable monomer (e.g., those to form polyamides, polyesters or polyurethanes), and a ring-cleavable monomer (e.g., oxazoline or caprolactone-type ones).

Preferably, the component (A2) includes those containing at least one selected from the group consisting of the following component (A2-1) to (A2-4), more preferably those containing the component (A2-1).
(A2-1) An acryl silicone polymer.
(A2-2) A silicone-modified alicyclic structure-containing polymer.
(A2-3) A silicone-modified pullulan.
(A2-4) A polyurea/urethane silicone.
[Acryl Silicone Polymer (A2-1)]

The acryl silicone polymer of the component (A2-1) includes an acrylic polymer having a carbosiloxane dendrimer in the side chain, an acryl-silicone graft copolymer, and a graft-type copolymer or alternate block-type copolymer where a structural unit of a polysiloxane group and a structural unit of a polymer of an unsaturated monomer bond via a sulfide bond.

The acrylic polymer having a carbosiloxane dendrimer structure in the side chain includes a silicone dendrimer-acryl copolymer, and for example, can be produced according to the production method described in JP H11-1530 A and JP 2000-63225 A.

The acrylic polymer having a carbosiloxane dendrimer structure in the side chain is preferably, as INCI nomenclature, acrylates/polytrimethylsiloxymethacrylate copolymer. Commercial products thereof include DOWSIL FA 4001 CM Silicone Acrylate (30 mass % decamethylcyclopentasiloxane solution), DOWSIL FA 4002 ID Silicone Acrylate (40 mass % isododecane solution) (all by Dow Toray Corporation).

The acryl-silicone graft copolymer includes a radical polymer of an organopolysiloxane compound having a radical polymerizable group at one terminal of the molecular chain and a radical polymerizable monomer mainly composed of an acrylate and/or a methacrylate.

Examples of the radical polymer of an organopolysiloxane compound having a radical polymerizable group at one terminal of the molecular chain and a radical polymerizable monomer mainly composed of an acrylate and/or a methacrylate usable here include those described in JP H2-25411 A and JP H2-132141 A, and acryl-silicone graft copolymers described in JP H3-162442 A and JP 2003-104825 A.

The acryl-silicone graft copolymer is preferably, as INCI nomenclature, (acrylates/dimethicone) copolymer. Commercial products thereof include KP-545 (30 mass % decamethylcyclopentasiloxane solution), KP-549 (40 mass % methyltrimethicone solution), and KP-550 (40 mass % isododecane solution) (all by Shin-Etsu Chemical Industry Co., Ltd.).

The graft-type copolymer or alternate block-type copolymer where a structural unit of a polysiloxane group and a structural unit of a polymer of an unsaturated monomer bond via a sulfide bond include graft-type copolymers or alternate block-type copolymers described in JP H6-92825 A.

Above all, from the viewpoint of improving film formability and wash resistance, the component (A2-1) is preferably at least one selected from the group consisting of an acrylic polymer having a carbosiloxane dendrimer structure in the side chain and an acryl-silicone graft copolymer, more preferably at least one selected from (acrylates/polytrimethylsiloxymethacrylate) copolymer and (acrylates/dimethicone) copolymer.
[Silicone-Modified Alicyclic Structure-Containing Polymer (A2-2)]

Examples of the silicone-modified alicyclic structure-containing polymer include silicone-modified cyclic poly-olefins, and preferred examples thereof include silicone-modified polynorbornenes represented by the following general formula (A2-2-1).

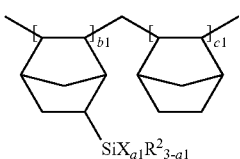

(A2-2-1)

wherein $R^2$ each independently represents an alkyl group having 1 or more and 12 or less carbon atoms, X represents a group represented by the following formula (i), a1 is an integer of 1 or more and 3 or less, b1 and c1 each are a repeating unit number, and are each independently an integer of 1 or more.

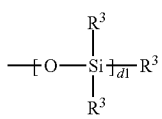

(i)

wherein $R^3$ each independently represents a hydrocarbon group having 1 or more and 12 or less carbon atoms, and d1 is an integer of 1 or more and 5 or less.

In the general formula (A2-2-1), $R^2$ is preferably a methyl group, an ethyl group, an n-propyl group, a butyl group or a pentyl group, more preferably a methyl group.

X is a group represented by the formula (i), and in the formula (i), $R^3$ each are independently a hydrocarbon group having 1 or more and 12 or less carbon atoms. $R^3$ is preferably an alkyl group having 1 or more and 12 or less or a phenyl group, more preferably an alkyl group having 1 or more and 3 or less carbon atoms, even more preferably a methyl group. d1 is an integer of 1 or more and 5 or less, and is, from the viewpoint of versatility, preferably d1=1. Specifically, X is preferably a trimethylsiloxy group.

a1 is an integer of 1 or more and 3 or less, and, for example, in the polymer, a repeating unit of a1=2 and a repeating unit of a1=3 may exist as mixed. From the viewpoint of versatility, a1 is preferably 3.

The proportion of b1 and c1 in the general formula (A2-2-1) is preferably b1/c1=20/80 to 90/10 (mol/mol), more preferably 30/70 to 80/20 (mol/mol), even more preferably 50/50 to 70/30 (mol/mol). The proportion of b1 and c1 can be determined by $^1$H-NMR measurement.

The silicone-modified polynorbornene is preferably a silicone-modified polynorbornene represented by the following formula (A2-2-2).

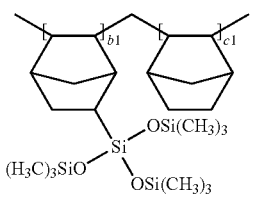

(A2-2-2)

wherein b1 and c1 are the same as above.

The silicone-modified polynorbornene represented by the general formula (A2-2-2) include a compound of, as INCI nomenclature, (norbornene/tris(trimethylsiloxy)silylnorbornene copolymer).

Commercial products of the silicone-modified polynorbornene include NBN-30-ID (isododecane solution of (norbornene/tris(trimethylsiloxy)silylnorbornene copolymer) (by Shin-Etsu Chemical Industry Co., Ltd.).

[Silicone-Modified Pullulan (A2-3)]

The silicone-modified pullulan includes a pullulan having a silicone structure in the side chain, and specifically preferred is a silicone-modified pullulan in which at least a part of the hydrogen atoms of the OH groups in pullulan are substituted with a group represented by the following general formula (ii).

$$—R^4—SiX_{a1}R^2_{3-a1} \qquad (ii)$$

wherein $R^4$ represents a single bond or a divalent organic group, and $R^2$, X and a1 are the same as above. From the viewpoint of versatility, X is preferably a trimethylsiloxyl group, and a1 is preferably 3.

In the general formula (ii), $R^4$ is preferably a divalent organic group, more preferably a divalent group represented by the following general formula (iii) or (iv), even more preferably a divalent group represented by the general formula (iv).

wherein $R^5$ represents an alkylene group having 1 or more and 10 or less carbon atoms, and examples thereof include a methylene group, an ethylene group, a trimethylene group, a propylene group and a butylene group. Among these, preferred are an ethylene group, a trimethylene group and a propylene group; and more preferred are a trimethylene group and a propylene group.

Commercial products of the silicone-modified pullulan include TSPL-30-ID (isododecane solution of tri(trimethylsiloxy)silylpropylcarbamate pullulan), and TSPL-30-D5 (cyclopentasiloxane solution of tri(trimethylsiloxy)silylpropylcarbamate pullulan) (all by Shin-Etsu Chemical Industry Co., Ltd.).

[Polyurea/Urethane Silicone (A2-4)]

The polyurea/urethane silicone of the component (A2-4) includes a polysiloxane/polyurea/polyurethane block terpolymer. For example, it is a dimethylpolysiloxane/urea copolymer of "polyurea-dimethicone" as INCI nomenclature.

The polymer can be produced by copolymerization of an α,ω-aminosilicone and a diisocyanate. Commercial products of the polyurea/urethane silicone include "Wacker-Belsil UD 60", "Wacker-Belsil UD 80", "Wacker-Belsil UD 140" and "Wacker-Belsil UD 200" (all by Wacker Corporation).

One or more can be used as the component (A). Among the above, from the viewpoint of improving film formability and durability, the component (A) preferably contains at least one selected from the group consisting of the component (A1), the component (A2-1) and the component (A2-2), more preferably contains at least one selected from the group consisting of the component (A1) and the component (A2-1), even more preferably contains at least one selected from the group consisting of the component (A1-2) and the component (A2-1), further more preferably contains the component (A1-2).

More specifically, from the viewpoint of improving film formability and durability, and from the viewpoint of providing a dirt adhesion preventing effect, a good feel and a high drying speed, the component (A) preferably contains at least one selected from the group consisting of trimethylsiloxysilicate, phenylpropyldimethylsiloxysilicate, trifluoropropyldimethyltrimethylsiloxysilicate, (trimethylsiloxysilicate/dimethiconol) crosspolymer, polymethylsilsesquioxane, polypropylsilsesquioxane, (acrylates/polytrimethylsiloxymethacrylate) copolymer, (acrylates/dimethicone) copolymer, and (norbornene/tris(trimethylsiloxy)silylnorbornene) copolymer, more preferably contains at least one selected from the group consisting of trimethylsiloxysilicate, phenylpropyldimethylsiloxysilicate, trifluoropropyldimethyltrimethylsiloxysilicate, (trimethylsiloxysilicate/dimethiconol) crosspolymer, polymethylsilsesquioxane, polypropylsilsesquioxane, (acrylates/polytrimethylsiloxymethacrylate) copolymer, and (acrylates/dimethicone) copolymer, and from the viewpoint of providing a high drying speed, even more preferably contains at least one selected from the group consisting of trimethylsiloxysilicate, trifluoropropyldimethyltrimethylsiloxysilicate, (trimethylsiloxysilicate/dimethiconol) crosspolymer, (acrylates/polytrimethylsiloxymethacrylate) copolymer and (acrylates/dimethicone) copolymer, further more preferably contains at least one selected from the group consisting of trimethylsiloxysilicate, trifluoropropyldimethyltrimethylsiloxysilicate and (trimethylsiloxysilicate/dimethiconol) crosspolymer, further more preferably contains at least one selected from trimethylsiloxysilicate and trifluoropropyldimethyltrimethylsiloxysilicate, further more preferably contains trimethylsiloxysilicate, and is further more preferably trimethylsiloxysilicate.

<Component (B): High-Molecular-Weight Organopolysiloxane>

The cosmetic composition of the present invention contains, as the component (B), a high-molecular-weight organopolysiloxane having a degree of polymerization of 2,600 or more and 4,500 or less. The cosmetic composition of the present invention contains the component (B) having a specific viscosity, and therefore, it is considered that when the composition is applied to the surface of a keratin substance such as skin or hair, it can suppress stickiness and can give a good feel and in addition, can give a dirt adhesion preventing effect.

The degree of polymerization of the component (B) is, from the viewpoint of, when applied to the surface of a keratin substance such as skin or hair, suppressing stickiness, and giving a good feel and also giving a dirt adhesion preventing effect, preferably 2,700 or more, more preferably 2,800 or more, even more preferably 2,900 or more, further more preferably 3,000 or more, further more preferably 3,100 or more, further more preferably 3,200 or more, and is, from the viewpoint of availability, preferably 4,300 or less, more preferably 4,200 or less, even more preferably 4,000 or less. A specific range of the degree of polymerization of the component (B) is 2,600 to 4,500, preferably 2,700 to 4,500, more preferably 2,800 to 4,300, even more preferably 2,900 to 4,200, further more preferably 3,000 to 4,200, further more preferably 3,00 to 4,000, further more preferably 3,100 to 4,000, further more preferably 3,200 to 4,000.

More precisely, the component (B) is preferably an organopolysiloxane represented by the following general formula (1).

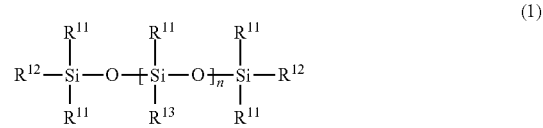

wherein $R^{11}$ each independently represents a hydrocarbon group having 1 or more and 6 or less carbon atoms, $R^{12}$ each independently represents a hydroxy group, an alkoxy group having 1 or more and 6 or less carbon atoms, or a hydrocarbon group having 1 or more and 6 or less carbon atoms, $R^{13}$ represents a hydrocarbon group having 1 or more and 6 or less carbon atoms, or a primary to tertiary amino group-containing group, n indicates a degree of polymerization, and is a number of 2,600 or more and 4,500 or less, and n's $R^{13}$'s can be the same as or different from each other.

In the formula (1), the hydrocarbon group for $R^H$ may be any of an aliphatic group or an aromatic group, and examples thereof include an alkyl group, an alkenyl group and a phenyl group. The alkyl group and the alkenyl group may be any of linear or branched ones.

Among the above, $R^{11}$ is preferably an alkyl group having 1 or more and 6 or less carbon atoms, or a phenyl group, more preferably an alkyl group having 1 or more and 3 or less carbon atoms or a phenyl group, even more preferably a methyl group or a phenyl group, further more preferably a methyl group.

In the general formula (1), $R^{12}$ each independently represent a hydroxy group, an alkoxy group having 1 or more and 6 or less carbon atoms, or a hydrocarbon group having 1 or more and 6 or less carbon atoms.

The alkoxy group for $R^{12}$ includes a methoxy group, an ethoxy group, a propoxy group and a butoxy group.

The hydrocarbon group for $R^{12}$ is the same as that for $R^{11}$, and is preferably an alkyl group having 1 or more and 6 or less carbon atoms, or a phenyl group, more preferably an alkyl group having 1 or more and 3 or less carbon atoms, or a phenyl group, even more preferably a methyl group or a phenyl group, further more preferably a methyl group.

$R^{12}$ is, from the viewpoint of providing a dirt adhesion preventing effect, a good feel and a high drying speed, preferably a hydroxy group, an alkyl group having 1 or more and 6 or less carbon atoms, or a phenyl group, more preferably a hydroxy group, an alkyl group having 1 or more and 3 or less carbon atoms, or a phenyl group, even more preferably a hydroxy group, a methyl group or a phenyl group, further more preferably a methyl group.

In the general formula (1), $R^{13}$ represents a hydrocarbon group having 1 or more and 6 or less carbon atoms, or a primary to tertiary amino group-containing group.

The hydrocarbon group for $R^{13}$ is the same as that for $R^{11}$, and is preferably an alkyl group having 1 or more and 6 or less carbon atoms, or a phenyl group, more preferably an alkyl group having 1 or more and 3 or less carbon atoms, or a phenyl group, even more preferably a methyl group or a phenyl group, further more preferably a methyl group.

The primary to tertiary amino group-containing group (hereinafter also referred to simply as "amino group-containing group") for $R^{13}$ is preferably a group represented by $—N(R^{14})_2$, $—NR^{14}(CH_2)_pN(R^{14})_2$, or $—NR^{14}(CH_2)_pN$ ($R^{15}$)CO—$R^{16}$. Here, $R^{14}$ represents a hydrogen atom or a monovalent hydrocarbon group having 1 or more and 4 or less carbon atoms, and is preferably a hydrogen atom, a methyl group or an ethyl group. $R^{15}$ represents a monovalent hydrocarbon group having 1 or more and 4 or less carbon atoms, and is preferably a methyl group or an ethyl group. $R^{16}$ represents a monovalent hydrocarbon group having 1 or more and 4 or less carbon atoms. p indicates a number of 2 or more and 6 or less, and is preferably a number of 2 or more and 4 or less.

The amino group-containing group for $R^{13}$ is preferably —$(CH_2)_3$—$NH_2$, —$(CH_2)_3$—$N(CH_3)_2$, —$(CH_2)_3$—NH—$(CH_2)_2$—$NH_2$, or —$(CH_2)_2$—NH—$(CH_2)_2$—$N(CH_3)_2$, more preferably —$(CH_2)_3$–$NH_2$.

From the viewpoint of providing a dirt adhesion preventing effect, a good feel and a high drying speed, $R^{13}$ is preferably a hydrocarbon group having 1 or more and 6 or less carbon atoms, more preferably an alkyl group having 1 or more and 6 or less carbon atoms or a phenyl group, even more preferably an alkyl group having 1 or more and 3 or less carbon atoms or a phenyl group, further more preferably a methyl group or a phenyl group, further more preferably a methyl group.

In the general formula (1), n indicates a degree of polymerization and is a number of 2,600 or more and 4,500 or less. From the viewpoint of preventing stickiness when applied to the surface of a keratin substance such as skin or hair, and giving a good feel and providing a dirt adhesion preventing effect, n is preferably 2,700 or more, more preferably 2,800 or more, even more preferably 2,900 or more, further more preferably 3,000 or more, further more preferably 3,100 or more, further more preferably 3,200 or more, and is, from the viewpoint of availability, preferably 4,300 or less, more preferably 4,200 or less, even more preferably 4,000 or less. A specific range of n in the general formula (1) is 2,600 to 4,500, preferably 2,700 to 4,500, more preferably 2,800 to 4,300, even more preferably 2,900 to 4,200, further more preferably 3,000 to 4,200, further more preferably 3,000 to 4,000, further more preferably 3,100 to 4,000, further more preferably 3,200 to 4,200.

The viscosity of the component (B) is, from the viewpoint of preventing stickiness when applied to the surface of a keratin substance such as skin or hair, and giving a good feel and providing a dirt adhesion preventing effect, preferably 3,000,000 mm²/s or more, more preferably 5,000,000 mm²/s or more, even more preferably 8,000,000 mm²/s or more, further more preferably 10,000,000 mm²/s or more, further more preferably 15,000,000 mm²/s or more. The upper limit of the viscosity of the component (B) is, from the viewpoint of availability, preferably 125,000,000 mm²/s or less, more preferably 80,000,000 mm²/s or less, even more preferably 50,000,000 mm²/s or less, further more preferably 40,000,000 mm²/s or less, further more preferably 35,000,000 mm²/s or less.

A specific range of the viscosity of the component (B) is preferably 3,000,000 to 125,000,000 mm²/s, more preferably 3,000,000 to 80,000,000 mm²/s, even more preferably 3,000,000 to 50,000,000 mm²/s, further more preferably 3,000,000 to 40,000,000 mm²/s, further more preferably 3,000,000 to 35,000,000 mm²/s, further more preferably 5,000,000 to 35,000,000 mm²/s, further more preferably 8,000,000 to 35,000,000 mm²/s, further more preferably 10,000,000 to 35,000,000 mm²/s, further more preferably 15,000,000 to 35,000,000 mm²/s.

The viscosity is a value measured at 25° C. according to JIS Z8803:2011 "Method for Measurement of Viscosity of Liquid". For example, using a suitable one selected from a capillary viscometer, a falling ball viscometer, a rotational viscometer and a vibration-type viscometer, the viscosity can be measured. In the case where the viscosity oversteps an ordinary measurement range of a viscometer, it can be determined from a diluted solution of the component (B) according to the following method.

A toluene solution of the component (B) having a concentration of 1 g/100 mL is prepared, and a specific viscosity thereof ηsp (25° C.) is calculated according to the following mathematical expression (1). Next, the resultant value is introduced into the Huggins relational expression represented by the following mathematical expression (2) to give an intrinsic viscosity [η]. Further, [η] is introduced into the expression by A. Kolorlov represented by the following mathematical expression (3) to give a molecular weight M. Finally, M is introduced into the expression by A. J. Barry represented by the following mathematical expression (4) to give a viscosity η of the component (B). (For example, see Silicone Oil KF-96 Performance Test Results 4.2, by Shin-Etsu Chemical Industry Co., Ltd.).

$$\eta sp=(\eta/\eta 0)-1 \quad (1)$$

wherein η0 represents a viscosity of toluene, and η is a viscosity of the solution.

$$\eta sp=[\eta]+K'[\eta]^2 \quad (2)$$

wherein the Hoggins' constant K' is one described in Nakamuta, Nihon Kagakukai-shi, 77588 [1956].

$$[\eta]=0.215 \times 10^{-4} M^{0.65} \quad (3)$$

$$\log \eta=1.00+0.0123 M^{0.5} \quad (4)$$

Commercial products of the dimethylpolysiloxane used as the component (B) include X-21-5686 (viscosity 3,000,000 mm²/s), X-25-9074 (viscosity 30,000,000 mm²/s) (both by Shin-Etsu Chemical Industry Co., Ltd.), and Silsoft B3020 (viscosity 20,000,000 mm²/s) (by Momentive Performance Materials Corporation).

The component (B) is, from the viewpoint of providing a dirt adhesion preventing effect, a good feel and a high drying speed, preferably at least one selected from the group consisting of dimethylpolysiloxane, methylphenylpolysiloxane, aminopropylmethylpolysiloxane and dimethiconol, of which the degree of polymerization falls within the above-mentioned range, more preferably dimethylpolysiloxane of which the degree of polymerization falls within the range.

<Content>

The content of the component (A) in the cosmetic composition is, from the viewpoint of imparting a good feel to the surface of a keratin substance such as skin or hair, and from the viewpoint of increasing the drying speed, preferably 0.5% by mass or more, more preferably 1% by mass or more, even more preferably 2% by mass or more, further more preferably 3% by mass or more, and is, from the viewpoint of improving sustainability of various effects after washing, preferably 30% by mass or less, more preferably 25% by mass or less, even more preferably 20% by mass or less, further more preferably 15% by mass or less. A specific range of the content of the component (A) in the cosmetic composition of the present invention is preferably 0.5 to 30% by mass, more preferably 1 to 25% by mass, even more preferably 2 to 20% by mass, further more preferably 2 to 15% by mass, further more preferably 3 to 15% by mass.

The content of the component (B) in the cosmetic composition is, from the viewpoint of improving sustainability of various effects after washing, preferably 0.1% by mass or more, more preferably 0.3% by mass or more, even more preferably 0.5% by mass or more, further more preferably 1% by mass or more, and is, from the viewpoint of providing a dirt adhesion preventing effect and imparting a good feel to the surface of a keratin substance such as skin or hair, preferably 30% by mass or less, more preferably 25% by mass or less, even more preferably 20% by mass or less, further more preferably 15% by mass or less, further more preferably 10% by mass or less, further more preferably 8% by mass or less. A specific range of the content of the component (B) in the cosmetic composition of the present invention is preferably 0.1 to 30% by mass, more preferably 0.3 to 25% by mass, even more preferably 0.5 to 20% by mass, further more preferably 1 to 20% by mass, further more preferably 1 to 15% by mass, further more preferably 1 to 10% by mass, further more preferably 1 to 8% by mass.

The total content of the components (A) and (B) in the cosmetic composition of the present invention is, from the viewpoint of improving film formability and durability, preferably 1% by mass or more, more preferably 2% by mass or more, even more preferably 3% by mass or more, further more preferably 4% by mass or more, further more preferably 5% by mass or more, further more preferably 7% by mass or more. From the viewpoint of improving the dirt adhesion preventing effect, and from the viewpoint of providing a good feel, the total content is preferably 50% by mass or less, more preferably 40% by mass or less, even more preferably 30% by mass or less, further more preferably 25% by mass or less. A specific range of the total content of the components (A) and (B) in the cosmetic composition of the present invention is preferably 1 to 50% by mass, more preferably 2 to 40% by mass, even more preferably 3 to 30% by mass, further more preferably 4 to 30% by mass, further more preferably 5 to 30% by mass, further more preferably 7 to 30% by mass, further more preferably 7 to 25% by mass.

A ratio of the content by mass of the component (A) to the total content by mass of the component (A) and the component (B) in the cosmetic composition of the present invention, [(A)/((A)+(B))] is, from the viewpoint of improving the dirt adhesion preventing effect, 50% or more, preferably 55% or more, more preferably 60% or more. From the viewpoint of improving sustainability of various effects after washing, the ratio is 98% or less, preferably 95% or less. A specific range of the ratio of the content by mass of the component (A) to the total content by mass of the component (A) and the component (B) in the cosmetic composition of the present invention, [(A)/((A)+(B))] is, 50 to 98%, preferably 55 to 98%, more preferably 60 to 98%, further more preferably 60 to 95%.

<Component (C): Solvent>

From the viewpoint of dissolving or dispersing the component (A), the component (B) and other components, and from the viewpoint of controlling the viscosity to be easily applicable to a keratin substance such as skin or hair, the cosmetic composition of the present invention can further contain a solvent as a component (C).

The solvent is, from the viewpoint of easy handleability, preferably a liquid organic solvent, including an alcohol solvent, an ether solvent, a ketone solvent, an ester solvent, a hydrocarbon solvent and a silicone solvent, and these can be appropriately selected depending on the formulation form. Among these, from the viewpoint of bettering sense of use after drying (from the viewpoint of reducing stickiness), a volatile solvent is preferably contained.

Among volatile solvents, the alcohol solvent includes ethanol, 1-propanol, 2-propanol, 1-butanol, 2-butanol and benzyl alcohol; the ether solvent includes diethyl ether, and tetrahydrofuran; the ketone solvent includes acetone, and methyl ethyl ketone; the ester solvent includes methyl acetate, ethyl acetate, butyl acetate and isobutyl acetate; the hydrocarbon solvent includes light liquid isoparaffin (containing, as a main component, isoparaffin having 8 to 16 carbon atoms), pentane, isopentane, hexane, isohexene, heptane, isoheptane, decane, isodecane, dodecane, isododecane, tridecane, isotridecane, tetradecane, and isotetradecane; the silicone solvent includes a cyclic silicone such as decamethylcyclopentasiloxane, dimethylpolysiloxane having a viscosity at 25° C. of 10 mm$^2$/s or less, alkyltrimethicone such as methyltrimethicone, and methylphenylpolysiloxane having a viscosity at 25° C. of 20 mm$^2$/s or less. One or more of these can be used.

From solubility of the component (A) and the component (B) therein, the component (C) preferably contains at least one selected from the group consisting of dimethylpolysiloxane having a viscosity at 25° C. of 10 mm$^2$/s or less, methyltrimethicone, methylphenylpolysiloxane having a viscosity at 25° C. of 20 mm$^2$/s or less, pentane, isopentane, hexane, isohexene, heptane, isoheptane, decane, isodecane, dodecane, isododecane, tridecane, isotridecane, tetradecane, isotetradecane and light liquid isoparaffin, more preferably at least one selected from the group consisting of dimethylpolysiloxane having a viscosity at 25° C. of 5 mm$^2$/s or less, methyltrimethicone, isodecane, isododecane, isotetradecane and light liquid isoparaffin, even more preferably at least one selected from the group consisting of isodecane, isododecane, isotetradecane and light liquid isoparaffin.

From the viewpoint of maintaining good solubility of the component (A) and the component (B) therein, and from the viewpoint of controlling the speed for film formation, the component (C) preferably contains a volatile alcohol solvent and at least one of a volatile hydrocarbon solvent or a volatile silicone solvent, more preferably contains at least one selected from the group consisting of ethanol, 1-propanol, 2-propanol, 1-butanol and 2-butanol, and at least one selected from the group consisting of dimethylpolysiloxane having a viscosity at 25° C. of 10 mm$^2$/s or less, methyltrimethicone, methylphenylpolysiloxane having a viscosity at 25° C. of 20 mm$^2$/s or less, pentane, isopentane, hexane, isohexene, heptane, isoheptane, decane, isodecane, dodecane, isododecane, tridecane, isotridecane, tetradecane, isotetradecane, and light liquid isoparaffin, even more preferably contains ethanol and at least one selected from the group consisting of dimethylpolysiloxane having a viscosity at 25° C. of 5 mm$^2$/s or less, methyltrimethicone, isodecane, isododecane, isotetradecane and light liquid isoparaffin, further more preferably contains ethanol and at least one selected from the group consisting of isodecane, isododecane, isotetradecane and light liquid isoparaffin.

In the case where the cosmetic composition of the present invention contains the component (C), the content thereof is, from the viewpoint of dissolving or dispersing the component (A) and the component (B) and other components, and from the viewpoint of improving drying speed, preferably 40% by mass or more in the cosmetic composition, more preferably 50% by mass or more, even more preferably 60% by mass or more, and is, from the viewpoint of controlling the viscosity of the cosmetic composition to be easily applicable to keratin substances such as skin or hair, preferably 99% by mass or less, more preferably 98% by mass or less. A specific range of the content of the solvent (C) in the cosmetic composition of the present invention is preferably 40 to 99% by mass, more preferably 50 to 99% by mass, even more preferably 60 to 98% by mass.

<Component (D): Functional Powder>

The cosmetic composition of the present invention can further contain a functional powder as a component (D), depending on the product form thereof.

In the present invention, the functional powder means a powder capable of providing various characteristics such as coloring performance, concealing performance, gloss, UV scattering, and feel controlling. In the case where the cosmetic composition of the present invention is a sunscreen cosmetic material, preferably, a UV scattering agent is incorporated therein as the component (D), from the viewpoint of providing a desired sunscreen effect. In the case where the cosmetic composition of the present invention is a makeup cosmetic composition or a hair dye composition, preferably, a pigment is incorporated therein as the component (D), from the viewpoint of providing a desired color tone.

As the UV scattering agent, preferably usable is at least one metal oxide powder selected from the group consisting of zinc oxide, titanium oxide and cerium oxide. An average particle size of the fine particle metal oxide powder is, from the viewpoint of UV protective effect, preferably 100 to 500 nm, more preferably 12 to 100 nm, even more preferably 15 to 50 nm. The average particle size can be measured according to a laser diffraction/scattering method.

The pigment may be any pigment generally used in makeup cosmetic materials and hair dye compositions, and examples thereof include a white inorganic pigment such as titanium oxide, zinc oxide, cerium oxide and barium sulfate; a colored inorganic pigment such as yellow iron oxide, black iron oxide, red iron oxide, carbon black, chromium oxide, chromium hydroxide, Prussian blue and ultramarine blue; a luster powder such as titanium oxide-coated mica, titanium oxide-coated bismuth oxychloride, iron oxide-coated mica titanium, iron oxide mica, Prussian blue-processed mica titanium, carmine-processed mica titanium, bismuth oxychloride, and fish scale guanine; an organic pigment such as Red No. 201, Red No. 202, Red No. 205, Red No. 226, Red No. 228, Orange No. 203, Orange No. 204, Blue No. 404, and Yellow No. 401; a chelate pigment such as a zirconium, barium or aluminum chelate of Red No. 3, Red No. 104, Red No. 106, Orange No. 205, Yellow No. 4, Yellow No. 5, Green No. 3 or Blue No. 1; and a composite pigment such as fine particle titanium oxide-coated mica titanium, fine particle zinc oxide-coated mica titanium, barium sulfate-coated mica titanium, titanium oxide-containing silicon dioxide and zinc oxide-containing silicon dioxide. One or more of these can be used either singly or as combined. Those prepared by coating the surfaces of these functional powders with various surface treatment agents are also usable as pigment. The surface treatment agent is not specifically limited. Various surface treatments can be applied to the powders, and examples thereof include fluorine compound treatment, silicone treatment, silicone resin treatment, pendant treatment, silane coupling agent treatment, titanium coupling agent treatment, oil treatment, metal soap treatment, N-acylated lysine treatment, polyethylene glycol treatment, PVA treatment, polyacrylic acid treatment, hyaluronic acid treatment, alginic acid treatment, inorganic compound treatment, plasma treatment and mechanochemical treatment, and the powders can be previously surface-treated by any of these treatments.

In the case where the cosmetic composition of the present invention contains the component (D), the content thereof is, from the viewpoint of providing desired performance, preferably 0.01% by mass or more in the cosmetic composition, more preferably 0.1% by mass or more, even more preferably 0.2% by mass or more, further more preferably 0.3% by mass or more, further more preferably 0.5% by mass or more, further more preferably 1% by mass or more, and is, from the viewpoint of dispersibility in the cosmetic composition and economic efficiency, and from the viewpoint of maintaining a good eel, preferably 50% by mass or less, more preferably 30% by mass or less. A specific range of the content of the component (D) in the cosmetic composition of the present invention is preferably 0.01 to 50% by mass, more preferably 0.1 to 50% by mass, even more preferably 0.2 to 30% by mass, further more preferably 0.3 to 30% by mass.

The cosmetic composition of the present invention can contain components generally used in cosmetic compositions, for example, an oily agent other than the above-mentioned components, an antioxidant, a fragrance, a colorant, a dye, a preservative, a thickener, a pH regulator, a blood circulation promoter, a cooling sensation agent, an antiperspirant, a bactericide, a skin activator, a moisturizer and a refrigerant, in addition to the above-mentioned components.

The cosmetic composition of the present invention can be produced according to an ordinary method.

From the viewpoint of a dirt adhesion preventing effect, a good feel and improvement of sustainability of various effects after washing, the water content in the cosmetic composition of the present invention is 10% by mass or less, preferably 5% by mass or less, more preferably less than 5% by mass, even more preferably less than 2% by mass.

From the viewpoint of a dirt adhesion preventing effect, a good feel and improvement of sustainability of various effects after washing, the content of the solid oil in the cosmetic composition of the present invention is preferably small. The solid oil is an oil that is solid at 25° C., and includes a solid paraffin such as paraffin wax, a polyolefin wax such as polyethylene wax, and beeswax. The content is preferably less than 50% by mass in the cosmetic composition, more preferably less than 20% by mass, even more preferably less than 10% by mass, further more preferably less than 5% by mass, further more preferably less than 1% by mass.

In the cosmetic composition of the present invention, the content of a nonvolatile liquid oily agent except the component (B) is preferably smaller, from the viewpoint of providing a dirt adhesion preventing effect, a good feel and a high drying speed, and from the viewpoint of improving sustainability of various effects after washing. The nonvolatile liquid oily agent is an oily agent that has a boiling point of higher than 260° C. under normal pressure and is liquid at 25° C., and examples thereof include a nonvolatile liquid silicone except the component (B); a triglyceride such as glyceryl trioctanoate, avocado oil, olive oil, sesame oil, rice bran oil, safflower oil, soybean oil, corn oil, rapeseed oil, castor oil, cotton seed oil, and mink oil; a fatty acid such as oleic acid and isostearic acid; an ester oil such as isopropyl myristate, butyl myristate, isopropyl palmitate, ethyl oleate, ethyl linoleate, isopropyl linoleate, cetyl caprylate, hexyl laurate, decyl myristate, decyl oleate, oleyl oleate, isostearyl laurate, isotridecyl myristate, isocetyl myristate, isostearyl myristate, octyl dodecyl myristate, octyl palmitate, isocetyl palmitate, isostearyl palmitate, isodecyl oleate, isopropyl isostearate, cetyl 2-ethylhexanoate, stearyl 2-ethylhexanoate, propylene glycol dicaprylate, propylene glycol dioleate, glyceryl tri-2-ethylhexanoate, glyceryl tri(caprate/caprylate), isononyl isononanoate, diisopropyl sebacate, propylene glycol isostearate, 2-ethylhexyl paramethoxycinnamate, 2-ethoxyethyl paramethoxycinnamate, isopropyl paramethoxycinnamate/diisopropylcinnamate mixture, methylbis(trimethylsiloxy)silylisopentyl trimethoxycinnamate, amyl paradimethylaminobenzoate, 2-ethylhexyl paradimethylaminobenzoate, ethylene glycol salicylate, 2-ethylhexyl salicylate, benzyl salicylate, homomenthyl salicylate, octocrylene, and dimethyldiethylbenzal malonate; and a branched or unsaturated higher alcohol such as 2-octyldodecanol, isostearyl alcohol, and oleyl alcohol. The content thereof is, in the cosmetic composition, preferably less than 50% by mass, more preferably less than 40% by mass, even more preferably less than 30% by mass, further more preferably less than 20% by mass, further more preferably less than 10% by mass.

From the viewpoint of the drying speed after application, the content of a volatile cyclic silicone such as decamethylcyclopentasiloxane in the cosmetic composition of the present invention is preferably small. This is because a volatile silicone oil takes a longer time for evaporation than a volatile hydrocarbon oil, and tends to prolong the time to be taken until drying after application to skin or hair. The content of a volatile cyclic silicone in the cosmetic composition is, from the viewpoint of increasing the drying speed after application, preferably less than 5% by mass in the cosmetic composition, more preferably less than 2% by mass, even more preferably less than 1% by mass, further more preferably less than 0.5% by mass, further more preferably less than 0.1% by mass, further more preferably 0% by mass.

From the viewpoint of providing a dirt adhesion preventing effect, a good feel and a high drying speed, and from the viewpoint of improving sustainability of various effects after washing, the content of a polyalcohol in the cosmetic composition of the present invention is preferably small. The polyalcohol includes a polyalcohol having a boiling point of higher than 260° C. under normal pressure, and examples thereof include propylene glycol and glycerin. The content is preferably less than 5% by mass in the cosmetic composition, more preferably less than 2% by mass, even more preferably less than 1% by mass, further more preferably less than 0.5% by mass, further more preferably less than 0.1% by mass.

<Formulation Form, Etc.>

The formulation form of the cosmetic composition of the present invention is not specifically limited, and depending on the product form thereof, the cosmetic composition can have various formation forms such as liquid, paste, cream, gel, foam, spray and wax. The cosmetic composition of the present invention is preferably a waterless composition. Here, the waterless composition means a composition having a water content of less than 1% by mass, preferably less than 0.5% by mass, more preferably less than 0.1% by mass.

The cosmetic composition of the present invention includes various skin cosmetic compositions, eyebrow or eyelash makeup compositions and hair cosmetic compositions.

The skin cosmetic composition includes various skin cosmetic compositions for makeup, foundation, skincare, sunscreen, etc.

The eyebrow or eyelash makeup composition includes various eyebrow or eyelash makeup compositions such as mascara, mascara base coat, mascara topcoat, and eyebrow mascara.

The hair cosmetic composition includes a hair wash composition such as shampoo, as well as a rinse composition, a conditioner composition, a treatment composition (including non-washing type), a styling composition, a hair dye composition, and a hair tonic composition. Among these, from the viewpoint of the effectiveness of the advantageous effects of the present invention, preferred are a conditioner composition, a treatment composition, a styling composition and a hair dye composition.

The above-mentioned composition is preferably a so-called leave-on preparation that is used without washing after application to keratin substances such as skin, eyebrow, eyelash or hair.

[Cosmetic Kit]

The present invention provides a cosmetic kit provided with the following compositions (I) and (II).

(I) A composition containing (A) a silicone film-forming agent.

(II) A composition containing (B) a high-molecular-weight organopolysiloxane having a degree of polymerization of 2,600 or more and 4,500 or less.

Preferred is a cosmetic kit in which a ratio by mass of the content of the component (A) to the total content of the component (A) and the component (B) contained in the compositions (I) and (II), [(A)/((A)+(B))] is 50% or more and 98% or less, and the water content is 10% by mass or less. The cosmetic kit of the present invention may be further provided with a composition containing neither the component (A) nor the component (B).

The cosmetic kit of the present invention is provided with the above-mentioned components (I) and (II), and before use, the compositions can be mixed and applied to a keratin substance such as skin, eyebrow or eyelash, or hair.

The component (A), the component (B) for use in the cosmetic kit and preferred embodiments thereof are the same as those in the cosmetic composition described hereinabove.

The compositions constituting the cosmetic kit can optionally contain, as needed, the solvent (C), the functional powder (D) and other optional components exemplified hereinabove for the cosmetic composition.

The concentration of each composition constituting the cosmetic kit is not specifically limited, but is preferably such that the ratio by mass of the content of of the component (A) to the total content of the component (A) and the component (B) contained in the compositions (I) and (II), [(A)/((A)+(B))] is 50% or more and 98% or less, and the total water content in the compositions (I) and (II) is 10% by mass or less. Namely, it is preferable that the ratio by mass of the content of the component (A) to the total content of the component (A) and the component (B) in the cosmetic composition to be obtained by mixing all the compositions constituting the cosmetic kit and the water content each could fall within the above range.

The by mass of the content of the component (A) to the total content of the component (A) and the component (B) in the cosmetic composition, [(A)/((A)+(B))] is preferably 55% or more, more preferably 60% or more, and is preferably 95% or less.

The water content in the cosmetic composition is 10% by mass or less, preferably 5% by mass or less, more preferably less than 5% by mass, even more preferably less than 2% by mass, further more preferably less than 1% by mass, further more preferably less than 0.5% by mass, further more preferably less than 0.1% by mass.

[Treatment Method for Keratin Substances]

From the viewpoint that the cosmetic composition of the present invention can promptly form a film excellent in an effect of preventing adhesion of dirt to the surface of a keratin substance and excellent in washing durability, the present invention also provides a treatment method for keratin substances, including a step of applying the cosmetic composition of the present invention to a keratin substance and then drying it.

The keratin substance includes skin, eyebrow, eyelash, hair and nails, and is preferably skin, eyelash, eyebrow or hair, more preferably hair. The keratin substance to which the cosmetic composition is applied may be in any of a dry state or wet state, but from the viewpoint of attaining the effects of the present invention, the cosmetic composition is preferably applied to a keratin substance in a dry state.

From the viewpoint of uniform application, and from the viewpoint of improving the uniformity of the structure of the film to be formed, it is preferable that the cosmetic composition of the present invention is temporarily compatibilized or dispersed prior to application to keratin substances, and then applied to the surfaces of keratin substances. As the temporarily compatibilizing or dispersing method, arbitrarily employable is any of a thermodynamical method of heating, a physical method of mechanically imparting shear stress, or a chemical method of adding a compatible solvent. From the viewpoint of user-friendliness, preferably, the cosmetic composition is uniformly compatibilized or dispersed by a physical method of stirring or shaking.

In the case where the cosmetic composition of the present invention is a skin cosmetic composition, or an eyebrow or eyelash cosmetic composition, preferably, the composition is applied to skin, eyebrow or eyelash and then spontaneously dried. From the viewpoint of maintaining various effects of the skin cosmetic composition, it is preferable that the composition is not washed off after drying, and is used as a leave-on preparation.

The skin cosmetic composition and the eyebrow or eyelash cosmetic composition is, after applied to skin, preferably dried before being brought into contact with clothes and other articles. The drying time is not specifically limited so far as, after the skin cosmetic composition has been applied, it can substantially form a film on the surface of skin, eyebrow or eyelash, and the time can be appropriately controlled depending on the coating amount and the coating area, and preferably, the formed film is dried for 4 minutes or less, more preferably 2 minutes or less.

In the case where the cosmetic composition of the present invention is a hair cosmetic composition, from the viewpoint of promptly forming a film excellent in a dirt adhesion preventing effect and washing durability on the surface of a keratin substance, it is preferable that the application process includes a step of applying the composition to hair and then drying it. From the viewpoint of maintaining various effects of the hair cosmetic composition, it is preferable that the composition is applied to hair in a dry state and then dried, and is used as a leave-on preparation that is not washed off after application. Drying the hair after application of the hair cosmetic composition thereto may be spontaneous drying, or the hair may be dried using a device such as a hair drier hood, a hand hair drier, or a straight iron.

In the case of using the device, preferably, the hair is dried at a temperature of 40 to 220° C. from the viewpoint of suppressing thermal damages of keratin substances. More preferred is drying with a hair drier hood or a hand hair drier, and the drying temperature is preferably 40 to 110° C., more preferably 50 to 90° C.

The drying time is not specifically limited so far as a film is substantially formed on the surface of hair, and can be appropriately controlled depending on the amount and the quality of hair. For example, the time may fall within a range of 10 seconds to 120 minutes.

After drying, the hair may be brushed to be straggly.

In the treatment method of the present invention, the amount of the cosmetic composition to be applied to keratin substances is not specifically limited. In the case of a skin cosmetic composition, in general, the amount falls within a range of 0.1 to 1000 mg per cm$^2$ of skin. In the case of an eyebrow or eyelash cosmetic composition or a hair cosmetic composition, in general, the amount falls within a range of 0.005 to 1 g per gram of eyebrow, eyelash or hair.

[Hair Dyeing Method]

From the viewpoint of promptly forming a film excellent in a dirt adhesion preventing effect and wash resistance on the surface of a keratin substance, the present invention further provides a hair dyeing method that includes a step of applying the hair dye composition of the present invention to hair and then drying it.

The hair dye composition of the present invention is applied to hair and then dried, and is used without washing. Drying the hair after applying the hair dye composition thereto may be spontaneous drying, or the hair may be dried with a drier or the like.

By the above-mentioned simple operation, the hair dye composition of the present invention can temporarily or semi-permanently dye hair as an out-bath treatment. In addition, the composition can give a dirt adhesion preventing effect, a good feel and a high drying speed to hair, and even after shampooing, the composition is still excellent in sustainability of these effects and secures good color duration without discoloration by shampooing.

Regarding the above-mentioned embodiments, the present invention discloses the following.

<1>

A cosmetic composition containing:
(A) a silicone film-forming agent, and
(B) a high-molecular-weight organopolysiloxane having a degree of polymerization of 2,600 or more and 4,500 or less, wherein:
a ratio by mass of the content of the component (A) to the total content of the component (A) and the component (B), [(A)/((A)+(B))] is 50% or more and 98% or less, and the water content is 10% by mass or less.

<2>

A cosmetic composition containing:
(A) a silicone film-forming agent, and
(B) a high-molecular-weight organopolysiloxane having a degree of polymerization of 2,800 or more and 4,300 or less, wherein:
a ratio by mass of the content of the component (A) to the total content of the component (A) and the component (B), [(A)/((A)+(B))] is 60% or more and 98% or less,
the total content of the component (A) and the component (B) is 3% by mass or more and 30% by mass or less, and
the water content is 10% by mass or less.

<3>

A cosmetic composition containing:
(A) a silicone film-forming agent, and
(B) a high-molecular-weight organopolysiloxane having a degree of polymerization of 3,000 or more and 4,000 or less, wherein:
a ratio by mass of the content of the component (A) to the total content of the component (A) and the component (B), [(A)/((A)+(B))] is 60% or more and 98% or less,
the total content of the component (A) and the component (B) is 7% by mass or more and 30% by mass or less, and
the water content is 10% by mass or less.

<4>
A cosmetic composition containing:
(A) a silicone film-forming agent containing at least one selected from the group consisting of the following component (A1) and component (A2-1),
(A1) a silicone resin represented by an average formula,
$(R^1)_m SiO_{(4-m)/2}$
wherein $R^1$ represents a hydrocarbon group having 1 or more and 12 or less carbon atoms and optionally substituted with fluorine, or a hydroxy group, plural $R^1$'s can be the same as or different from each other, and m is an average number, representing a number of more than 0 and less than 3,
which contains at least one unit selected from the group consisting of a T unit represented by $R^1 SiO_{3/2}$ and a Q unit represented by $SiO_{4/2}$,
(A2-1) an acryl silicone polymer, and
(B) 0.1 to 20% by mass of an organopolysiloxane represented by the following general formula (1),

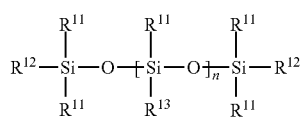

wherein $R^{11}$ each independently represents a hydrocarbon group having 1 or more and 6 or less carbon atoms, $R^{12}$ each independently represents a hydroxy group, an alkoxy group having 1 or more and 6 or less carbon atoms, or a hydrocarbon group having 1 or more and 6 or less carbon atoms, $R^{13}$ represents a hydrocarbon group having 1 or more and 6 or less carbon atoms, or a primary to tertiary amino group-containing group, n indicates a degree of polymerization, and is a number of 2,800 to 4,300, and n's $R^{13}$'s can be the same as or different from each other, wherein:
a ratio by mass of the content of the component (A) to the total content of the component (A) and the component (B), [(A)/((A)+(B))] is 60% or more and 98% or less,
the total content of the component (A) and the component (B) is 3% by mass or more and 30% by mass or less, and
the water content is 10% by mass or less.
<5>
A cosmetic composition containing:
(A) 0.5 to 25% by mass of a silicone resin represented by $[SiO_{4/2}]_c[(R^1)_3SiO_{1/2}]_d$ wherein c and d each are an average repeating unit number and c>0 and d>0, and
(B) 0.1 to 20% by mas of an organopolysiloxane represented by the following general formula (1),

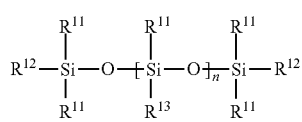

wherein $R^{11}$ each independently represents a hydrocarbon group having 1 or more and 6 or less carbon atoms, $R^{12}$ each independently represents a hydroxy group, an alkoxy group having 1 or more and 6 or less carbon atoms, or a hydrocarbon group having 1 or more and 6 or less carbon atoms, $R^{13}$ represents a hydrocarbon group having 1 or more and 6 or less carbon atoms, or a primary to tertiary amino group-containing group, n indicates a degree of polymerization, and is a number of 3,000 to 4,000, and n's RP's can be the same as or different from each other, wherein:
a ratio by mass of the content of the component (A) to the total content of the component (A) and the component (B), [(A)/((A)+(B))] is 60% or more and 98% or less,
the total content of the component (A) and the component (B) is 7% by mass or more and 30% by mass or less, and
the water content is 10% by mass or less.
<6>
The cosmetic composition of any one of <1> to <3>, wherein the component (A) is at least one selected from the group consisting of the following components (A1) and (A1),
(A1) a silicone resin represented by an average formula,
$(R^1)_m SiO_{(4-m)/2}$
wherein $R^1$ represents a hydrocarbon group having 1 or more and 12 or less carbon atoms and optionally substituted with fluorine, or a hydroxy group, plural $R^1$'s can be the same as or different from each other, and m is an average number, representing a number of more than 0 and less than 3,
which contains at least one unit selected from the group consisting of a T unit represented by $R^1 SiO_{3/2}$ and a Q unit represented by $SiO_{4/2}$,
(A2) a silicone polymer containing a polysiloxane moiety and a moiety formed of a non-silicone organic chain.
<7>
The cosmetic composition according to <4> or <6>, wherein the component (A1) contains at least one selected from the group consisting of the following component (A1-1) and component (A1-2),
(A1-1) a silicone resin represented by the above-mentioned average formula, containing a T unit represented by $R^1 SiO_{3/2}$ and substantially not containing a Q unit represented by $SiO_{4/2}$,
(A1-2) a silicone resin represented by the above-mentioned average formula, and containing a Q unit represented by $SiO_{4/2}$ and an M unit represented by $(R^1)_3 SiO_{1/2}$.
<8>
The cosmetic composition according to <6>, wherein the component (A2) contains at least one selected from the group consisting of the following component (A2-1) to (A2-4),
(A2-1) an acryl silicone polymer,
(A2-2) a silicone-modified alicyclic structure-containing polymer,
(A2-3) a silicone-modified pullulan,
(A2-4) a polyurea/urethane silicone.
<9>
The cosmetic composition according to any one of <4> and <6> to <8>, wherein the component (A1) contains the component (A1-2).
<10>
The cosmetic composition according to any one of <6> to <9>, wherein the component (A2) contains the acryl silicone polymer (A2-1).
<11>
The cosmetic composition according to any one of <1> to <4>, and <6> to <10>, wherein the component (A) contains at least one selected from the group consisting of trimethylsiloxysilicate, phenylpropyldimethylsiloxysilicate, trifluoropropyldimethyltrimethylsiloxysilicate, (trimethylsiloxysilicate/dimethiconol) crosspolymer, polymethylsilsesquioxane, polypropylsilsesquioxane, (acrylates/polytrimethylsiloxymethacrylate) copolymer, (acrylates/dimethicone) copolymer, and (norbornene/tris(trimethylsiloxy)silylnorbornene) copolymer, preferably contains at least one selected from the group consisting of trimethylsiloxysilicate, phenylpropyldimethylsiloxysilicate, trifluoropropyldimethyltrimethylsiloxysilicate, (trimethylsiloxysilicate/dimethiconol) crosspolymer, polymethylsilsesquioxane, polypropylsilsesquioxane, (acrylates/polytrimethylsiloxymethacrylate) copolymer, and (acrylates/dimethicone) copolymer, more preferably contains at least one selected from the group consisting of trimethylsiloxysilicate, trifluoropropyldimethyltrimethylsiloxysilicate, (trimethylsiloxysilicate/dimethiconol) crosspolymer, and (acrylates/dimethicone) copolymer, even more preferably contains at least one selected from the group consisting of trimethylsiloxysilicate, and trifluoropropyldimethyltrimethylsiloxysilicate, further more preferably contains trimethylsiloxysilicate, and is further more preferably trimethylsiloxysilicate.

<12>

The cosmetic composition according to any one of <1>, and <6> to <11>, wherein the component (B) is an organopolysiloxane represented by the following general formula (1),

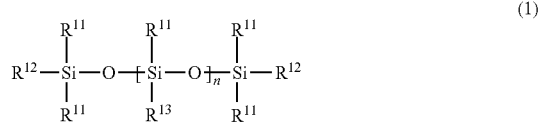

wherein $R^{11}$ each independently represents a hydrocarbon group having 1 or more and 6 or less carbon atoms, $R^{12}$ each independently represents a hydroxy group, an alkoxy group having 1 or more and 6 or less carbon atoms, or a hydrocarbon group having 1 or more and 6 or less carbon atoms, $R^{13}$ represents a hydrocarbon group having 1 or more and 6 or less carbon atoms, or a primary to tertiary amino group-containing group, n indicates a degree of polymerization, and is a number of 2,600 or more and 4,500 or less, and n's $R^{13}$'s can be the same as or different from each other.

<13>

The cosmetic composition according to <12>, wherein the degree of polymerization n in the general formula (1) is preferably 2,700 to 4,500, more preferably 2,800 to 4,300, even more preferably 2,900 to 4,200, further more preferably 3,000 to 4,200, further more preferably 3,000 to 4,000, further more preferably 3,100 to 4,000, further more preferably 3,200 to 4,000.

<14>

The cosmetic composition according to any one of <1>, and <6> to <13>, wherein a ratio by mass of the content of the component (A) to the total content of the component (A) and the component (B) in the cosmetic composition, [(A)/((A)+(3))] is preferably 55 to 98%, more preferably 60 to 98%, even more preferably 60 to 95%.

<15>

The cosmetic composition according to any one of <1>, and <6> to <14>, wherein the total content of the component (A) and the component (B) in the cosmetic composition is preferably 1 to 50% by mass, more preferably 2 to 40% by mass, even more preferably 3 to 30% by mass, further more preferably 7 to 30% by mass, further more preferably 7 to 25% by mass.

<16>

The cosmetic composition according to any one of <1> to <4>, and <6> to <15>, wherein the content of the component (A) in the cosmetic composition is preferably 0.5 to 30% by mass, more preferably 1 to 25% by mass, even more preferably 2 to 20% by mass, further more preferably 2 to 15% by mass, further more preferably 3 to 15% by mass.

<17>

The cosmetic composition according to any one of <1> to <3>, and <6> to <16>, wherein the content of the component (B) in the cosmetic composition is preferably 0.1 to 30% by mass, more preferably 0.3 to 25% by mass, even more preferably 0.5 to 20% by mass, further more preferably 1 to 20% by mass, further more preferably 1 to 15% by mass, further more preferably 1 to 10% by mass, further more preferably 1 to 8% by mass.

<18>

The cosmetic composition according to any one of <1> to <17>, further containing a solvent as a component (C).

<19>

The cosmetic composition according to <18>, wherein the component (C) contains at least one selected from the group consisting of dimethylpolysiloxane having a viscosity at 25° C. of 10 mm$^2$/s or less, methyltrimethicone, methylphenylpolysiloxane having a viscosity at 25° C. of 20 mm$^2$/s or less, pentane, isopentane, hexane, isohexene, heptane, isoheptane, decane, isodecane, dodecane, isododecane, tetradecane, isotetradecane, tridecane, isotridecane, and light liquid isoparaffin, preferably at least one selected from the group consisting of dimethylpolysiloxane having a viscosity at 25° C. of 5 mm$^2$/s or less, methyltrimethicone, isodecane, isododecane, isotetradecane and light liquid isoparaffin, more preferably at least one selected from the group consisting of isodecane, isododecane, isotetradecane and light liquid isoparaffin.

<20>

The cosmetic composition according to <18> or <19>, wherein the component (C) preferably contains a volatile alcohol solvent and at least one of a volatile hydrocarbon solvent or a volatile silicone solvent, more preferably contains at least one selected from the group consisting of ethanol, 1-propanol, 2-propanol, 1-butanol and 2-butanol, and at least one selected from the group consisting of dimethylpolysiloxane having a viscosity at 25° C. of 10 mm$^2$/s or less, methyltrimethicone, methylphenylpolysiloxane having a viscosity at 25° C. of 20 mm$^2$/s or less, pentane, isopentane, hexane, isohexene, heptane, isoheptane, decane, isodecane, dodecane, isododecane, tridecane, isotridecane, tetradecane, isotetradecane, and light liquid isoparaffin, even more preferably contains ethanol and at least one selected from the group consisting of dimethylpolysiloxane having a viscosity at 25° C. of 5 mm$^2$/s or less, methyltrimethicone, isodecane, isododecane, isotetradecane and light liquid isoparaffin, further more preferably contains ethanol and at least one selected from the group consisting of isodecane, isododecane, isotetradecane and light liquid isoparaffin.

<21>

The cosmetic composition according to any one of <18> to <20>, wherein the content of the component (C) in the cosmetic composition is preferably 40 to 99% by mass, more preferably 50 to 99% by mass, even more preferably 60 to 98% by mass.

<22>
The cosmetic composition according to any one of <1> to <21>, further containing a functional powder as a component (D).
<23>
The cosmetic composition according to <22>, wherein the content of the component (D) in the cosmetic composition is preferably 0.01 to 50% by mass, more preferably 0.1 to 50% by mass, even more preferably 0.2 to 30% by mass, further more preferably 0.3 to 30% by mass.
<24>
The cosmetic composition according to any one of <1> to <23>, which is a hair cosmetic composition.
<25>
The cosmetic composition according to any one of <1> to <23>, which is a hair dye composition.
<26>
A method for treating a keratin substance, including a step of applying the cosmetic composition of any one of <1> to <23> to a keratin substance and then drying it.
<27>
A method for treating hair, including a step of applying the hair cosmetic composition of <24> to hair and then drying it.
<28>
A method for dyeing hair, including a step of applying the hair dye composition of <25> to hair and then drying it.
<29>
A cosmetic kit provided with the following compositions (I) and (II), (I) a composition containing (A) a silicone film-forming agent, (II) a composition containing (B) a high-molecular-weight organopolysiloxane having a degree of polymerization of 2,600 or more and 4,500 or less.
<30>
The cosmetic kit according to <29>, wherein:
the total content of the component (A) and the component (B) contained in the compositions (I) and (II) is 50% by mass or more and 98% by mass or less, and
the total content of water contained in the compositions (I) and (II) is 10% by mass or less.
<31>
A cosmetic kit provided with the following compositions (I) and (II),
(I) a composition containing (A) a silicone film-forming agent,
(II) a composition containing (B) a high-molecular-weight organopolysiloxane having a degree of polymerization of 2,800 or more and 4,300 or less, wherein:
a ratio by mass of the content of the component (A) to the total content of the component (A) and the component (B), [(A)/((A)+(B))] contained in the compositions (I) and (II) is 60% or more and 98% or less,
the total content of the component (A) and the component (B) contained in the compositions (I) and (II) is 3% by mass or more and 30% by mass or less, and
the water content contained in the compositions (I) and (II) is 10% by mass or less.
<32>
A cosmetic kit provided with the following compositions (I) and (II),
(I) a composition containing (A) a silicone film-forming agent,
(II) a composition containing (B) a high-molecular-weight organopolysiloxane having a degree of polymerization of 3,000 or more and 4,400 or less, wherein:
a ratio by mass of the content of the component (A) to the total content of the component (A) and the component (B), [(A)/((A)+(B))] contained in the compositions (I) and (II) is 60% or more and 98% or less,
the total content of the component (A) and the component (B) contained in the compositions (I) and (II) is 7% by mass or more and 30% by mass or less, and
the water content contained in the compositions (I) and (II) is 10% by mass or less.
<33>
A cosmetic kit provided with the following compositions (I) and (II),
(I) a composition containing (A) a silicone film-forming agent that contains at least one selected from the group consisting of the following component (A1) and component (A2-1),
(A1) a silicone resin represented by an average formula, $(R^1)_m SiO_{(4-m)/2}$
wherein $R^1$ represents a hydrocarbon group having 1 or more and 12 or less carbon atoms and optionally substituted with fluorine, or a hydroxy group, plural $R^1$'s can be the same as or different from each other, and m is an average number, representing a number of more than 0 and less than 3,
which contains at least one unit selected from the group consisting of a T unit represented by $R^1 SiO_{3/2}$ and a Q unit represented by $SiO_{4/2}$,
(A2-1) an acryl silicone polymer,
(II) a composition containing (B) an organopolysiloxane represented by the following general formula (1),

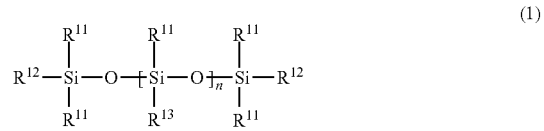

(1)

wherein $R^{11}$ each independently represents a hydrocarbon group having 1 or more and 6 or less carbon atoms, $R^{12}$ each independently represents a hydroxy group, an alkoxy group having 1 or more and 6 or less carbon atoms, or a hydrocarbon group having 1 or more and 6 or less carbon atoms, $R^{13}$ represents a hydrocarbon group having 1 or more and 6 or less carbon atoms, or a primary to tertiary amino group-containing group, n indicates a degree of polymerization, and is a number of 2,800 or more and 4,300 or less, and n's $R^{13}$'s can be the same as or different from each other,
wherein the content of the component (B) contained in the compositions (I) and (II) is 0.1 to 20% by mass,
a ratio by mass of the content of the component (A) to the total content of the component (A) and the component (B), [(A)/((A)+(B))] contained in the compositions (I) and (II) is 60% or more and 98% or less,
the total content of the component (A) and the component (B) contained in the compositions (I) and (II) is 3% by mass or more and 30% by mass or less, and
the water content contained in the compositions (I) and (II) is 10% by mass or less.
<34>
A cosmetic kit provided with the following compositions (I) and (II),
(I) a composition containing (A) a silicone resin represented by $[SiO_{4/2}]_c[(R^1)_3 SiO_{1/2}]_d$ wherein c and d each are an average repeating unit number and c>0 and d>0, and (B) a composition containing an organopolysiloxane represented by the following general formula (1),

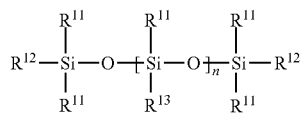

(1)

wherein $R^{11}$ each independently represents a hydrocarbon group having 1 or more and 6 or less carbon atoms, $R^{12}$ each independently represents a hydroxy group, an alkoxy group having 1 or more and 6 or less carbon atoms, or a hydrocarbon group having 1 or more and 6 or less carbon atoms, $R^{13}$ represents a hydrocarbon group having 1 or more and 6 or less carbon atoms, or a primary to tertiary amino group-containing group, n indicates a degree of polymerization, and is a number of 3,000 to 4,000, and n's $R^{13}$'s can be the same as or different from each other, wherein:

the content of the component (A) contained in the compositions (I) and (II) is 0.5 to 25% by mass, and the content of the component (B) is 0.1 to 20% by mass, a ratio by mass of the content of the component (A) to the total content of the component (A) and the component (B), [(A)/((A)+(B))] in the compositions (I) and (II) is 60% or more and 98% or less, the total content of the component (A) and the component (B) in the compositions (I) and (II) is 7% by mass or more and 30% by mass or less, and the water content in the compositions (I) and (II) is 10% by mass or less.

EXAMPLES

Hereinunder the present invention is described with reference to Examples, but the present invention is not restricted to the range of Examples. In these Examples, various measurements and evaluations were carried out according to the following methods.

<Preparation of Hair Bundles for Evaluation>

Human gray hair (100%) bundles (by Beaulax Co., Ltd., length 10 cm, mass 1 g) were shampooed with the following plain shampoo having a formulation mentioned below, then rinsed with warm water at 40° C., and fully dried to prepare hair bundles for evaluation.

(Plain Shampoo Formulation)

| Ingredient | (mass %) |
| --- | --- |
| Polyoxyethylene(2) lauryl ether sodium sulfate (*1) | 15.5 |
| Lauric acid diethanolamide (*2) | 1.5 |
| Tetrasodium edetate | 0.3 |
| Sodium benzoate | 1.43 |
| Pure water | balance |
| Total | 100.0 |

(*1): 57.4% by mass as Emal 227 (by Kao Corporation, active ingredient 27% by mass)
(*2): Aminon L-02 (by Kao Corporation)

<Difficulty of Dirt Adhesion>

15 µL of the hair cosmetic composition of each Example was dropwise applied to a commercial PET film (Lumirror Film T60-A4-100 µm by Toray Corporation), spread thereon with a bar coater (No. 3 by As One Corporation), spontaneously dried to form a coating film, and then the coating film part was cut out into a size of 3 cm×3 cm to prepare test films. The mass of the film is $F_0$ [g].

As a physical dirt model, zirconia beads ("YTZ ball" by Nikkato Co., Ltd., Φ=1 mm) were used. 10.4 g of zirconia beads were put into a balance dish (BD-2 by As One Corporation) and flattened, and the coated surface of the film that had been cut out into a size of 3 cm×3 cm was put thereon so as to be kept in contact therewith. Next, a balance dish was overlayed on the film, and further on this, a weight of 200 g prepared by putting tap water into a specified bottle (No. 11 by As One Corporation) was put and kept thereon for 30 seconds, and thereafter the weight was removed, and the mass of the beads-adhered film ($F_1$ [g]) was measured.

From the mass change before and after adhesion to beads, the beads adhesion ratio was calculated according to the following formula. The mass of beads to 100% cover the test film area of 3 cm×3 cm is 2.8367 g (average value in two-time measurement).

Beads Adhesion Ratio [%]=$(F_1-F_0$ [g])÷(mass of beads to 100% cover the test film area [g])×100

The above test was carried out two times, and an average value is shown in Table. An adhesion ratio of 30% or less can be said to mean difficulty of dirt adhesion, 25% or less can be more difficulty of dirt adhesion, 15% or less can be even more difficulty of dirt adhesion, and 5% or less can be further more difficulty of dirt adhesion.

<Feel in Dry State>

0.3 g of the hair cosmetic composition of each Example was applied to the hair bundle for evaluation, and then this was dried for 2 minutes with a drier ("P2-D250" by Hitachi Limited, setting HIGH) by applying hot air from a position separated by 18 cm from the hair bundle for hair treatment. Expert panelists organoleptically evaluated the feel of the treated hair bundles according to the following criteria, and a total point of N=3 was calculated. A total point of 5 or less means strong stickiness and non-smoothness. A total point of 6 means a smooth but sticky feel, a little good. A total point of 7 or more means a good feel, and a total point of 9 or more means a better feel.

4: Sticky little.
3: A little sticky.
2: Sticky.
1: Extremely sticky

<Feel in Dry State after 7-Time Shampooing>

The hair bundle treated in the same manner as above was shampooed with the plain shampoo having a formulation as above, rinsed with warm water at 40° C. and dried. The process was repeated 7 times. After shampooing 7 times, the feel of the dried hair bundle was organoleptically evaluated in the same manner as above.

<Drying Speed (Water Content after Rinsing)>

0.3 g of the hair cosmetic composition of each Example was applied to the hair bundle for evaluation, and then this was dried for 2 minutes with a drier ("P2-D250" by Hitachi Limited, setting HIGH) by applying hot air from a position separated by 18 cm from the hair bundle for hair treatment. After treated, the hair bundle was rinsed with warm water at about 40° C. for 30 seconds, then kept as such for 15 seconds and the water content W [%] was calculated according to the following formula.

Water content $W$ [%] after rinsing of treated hair bundle=$(a_2-a_1)÷a_0×100$ wherein:
$a_0$: weight [g] of untreated hair bundle
$a_1$: weight [g] of treated hair bundle
$a_2$: weight [g] of treated hair bundle after rinsing Further, a ratio X [%] of the water content W of the treated hair bundle after rinsing, relative to the water content ($W_0$) of the untreated hair bundle after rinsing (weight [g] of untreated hair bundle after rinsing−weight $a_0$ [g] of untreated hair bundle)/weight $a_0$ [g] of untreated hair bundle) was calculated according to the following formula.

$$X [\%] = W \div W_0 \times 100$$

A smaller X can be said to mean that the water content after rinsing is small relative to that of the untreated hair bundle and mean that the drying speed is high. X of 80% or less gives a feel of a rapid drying speed. 50% or less gives a feel of a more increased drying speed, 30% or less gives a feel of an even more increased drying speed, and 15% or less gives a feel of a further more increased drying speed.

<Drying Speed after 7-Time Shampooing (Water Content after Rinsing)>

The hair bundle treated in the same manner as above was shampooed with the plain shampoo having the formulation as above, and dried. The process was repeated 7 times. The hair bundle after 7-time shampooing was evaluated for the drying speed according to the same method as above.

<Shampooing Resistance (Difficulty of Discoloration in 7-Time Shampooing)

0.3 g of the hair cosmetic composition of Example 11 was applied to the hair bundle for evaluation, and then was dried for hair treatment.

The treated hair bundle was analyzed with a color difference meter (CR-400 by Konica Minolta, Inc.) in a CIE color system (L*,a*,b*). Then, this was shampooed with the plain shampoo having the formulation mentioned above, rinsed with warm water at 40° C. and dried. The process was repeated 7 times. After shampooing 7 times, the dried hair bundle was analyzed with the color difference meter in the same manner as above, and according to the following formulation, a color difference (ΔE*) from the hair bundle before shampooing was calculated. L*, a* and b* were measured at different 6 points on the hair bundle (each at 2 central points of each region obtained by equally dividing the hair bundle into three in the length direction), and the found data were averaged to give an average value.

$$\Delta E^* = \sqrt{(L_1^* - L_0^*)^2 + (a_1^* - a_0^*)^2 + (b_1^* - b_0^*)^2}$$

wherein:
$L_0^*, a_0^*, b_0^*$: found data of hair bundle before treatment (before shampooing),
$L_1^*, a_1^*, b_1^*$: found data of hair bundle after 7-time shampooing ΔE*<20 means that the treated hair is considered to have good shampooing resistance and to be excellent in color sustainability. ΔE*<15 means better, ΔE*<10 means even better and ΔE*<5 means further better.

Examples 1 to 11, Comparative Examples 1 to 2 (Preparation and Evaluation of Hair Cosmetic Composition)

Ingredients shown in Tables 1 to 5 were blended according to the formulation described in each Table, and then mixed until uniform to prepare hair cosmetic compositions. The resultant hair cosmetic compositions were evaluated according to the above-mentioned methods. The results are shown in Tables 1 to 5.

The blending amount (mass %) shown in Tables is an active ingredient amount.

TABLE 1

| | | (mass %) | Example 1 | Example 2 | Example 3 | Comparative Example 1 |
|---|---|---|---|---|---|---|
| (A) | (A1-2) Trimethylsiloxysilocate | X-21-5595 *1 | 6.6 | 8.0 | 11.4 | 4.0 |
| (B) | High-molecular weight dimethylpolysiloxane viscosity 20,000,000 mm²/s | Silsoft B3020 *2 | 5.4 | 4.0 | 0.6 | 8.0 |
| (C) | Isododecane | Marukasol R *3 | Balance | Balance | Balance | Balance |
| | Total | | 100 | 100 | 100 | 100 |
| | Total content of (A) + (B) (mass %) | | 12.0 | 12.0 | 12.0 | 12.0 |
| | Ratio by mass of content (A) in (A) + (B) (%) | | 55.0 | 66.7 | 95.0 | 33.3 |
| Evaluation Results | Difficulty of dirt adhesion | Adhesion ratio (%) of zirconia beads | 23.7 | 14.7 | 0.0 | 33.4 |
| | Feel in dry state | Non-stickiness | 9 | 9 | 12 | 8 |
| | Drying speed | Ratio of water content after rinsing of treated hair bundle, to water content after rinsing of untreated hair (%) | 47 | 9 | 5 | 42 |
| | Feel in dry state after 7-time shampooing | Non-stickiness | 9 | 9 | 12 | |
| | Drying speed after 7-time shampooing | Ratio of water content after rinsing of treated hair bundle, to water content after rinsing of untreated hair (%) | 36 | 23 | 28 | |

TABLE 2

| | (mass %) | | Example 4 | Example 2 | Example 5 | Comparative Example 2 |
|---|---|---|---|---|---|---|
| (A) | (A1-2) Trimethylsiloxysilocate | X-21-5595 *1 | 8.0 | 8.0 | 8.0 | 8.0 |
| (B) | High-molecular weight dimethylpolysiloxane viscosity 3,000,000 mm$^2$/s | X-21-5686 *4 | 4.0 | | | |
| | High-molecular weight dimethylpolysiloxane viscosity 20,000,000 mm$^2$/s | Silsoft B3020 *2 | | 4.0 | | |
| | High-molecular weight dimethylpolysiloxane viscosity 30,000,000 mm$^2$/s | X-25-9074 *5 | | | 4.0 | |
| (B') | High-molecular weight dimethylpolysiloxane viscosity 1,000,000 mm$^2$/s | KF-96H-1,000,000cs *6 | | | | 4.0 |
| (C) | Isododecane | Marukasol R *3 | Balance | Balance | Balance | Balance |
| | Total | | 100 | 100 | 100 | 100 |
| | Total content of (A) + (B) (mass %) | | 12.0 | 12.0 | 12.0 | 8.0 |
| | Ratio by mass of content (A) in (A) + (B) (%) | | 66.7 | 66.7 | 66.7 | 100.0 |
| Evaluation Results | Difficulty of dirt adhesion | Adhesion ratio (%) of zirconia beads | 6.8 | 14.7 | 14.5 | 6.6 |
| | Feel in dry state | Non-stickiness | 6 | 9 | 7 | 3 |
| | Drying speed | Ratio of water content after rinsing of treated hair bundle, to water content after rinsing of untreated hair (%) | 17 | 9 | 18 | 14 |
| | Feel in dry state after 7-time shampooing | Non-stickiness | 6 | 9 | 7 | |
| | Drying speed after 7-time shampooing | Ratio of water content after rinsing of treated hair bundle, to water content after rinsing of untreated hair (%) | 10 | 23 | 22 | |

TABLE 3

| | (mass %) | | Example 6 | Example 2 | Example 7 | Example 8 |
|---|---|---|---|---|---|---|
| (A) | (A1-2) Trimethylsiloxysilocate | X-21-5595 *1 | 1.33 | 8.0 | 13.335 | 26.67 |
| (B) | High-molecular weight dimethylpolysiloxane viscosity 20,000,000 mm$^2$/s | Silsoft B3020 *2 | 0.67 | 4.0 | 6.665 | 13.33 |
| (C) | Isododecane | Marukasol R *3 | Balance | Balance | Balance | Balance |
| | Total | | 100 | 100 | 100 | 100 |
| | Total content of (A) + (B) (mass %) | | 2.0 | 12.0 | 20.0 | 40.0 |
| | Ratio by mass of content (A) in (A) + (B) (%) | | 66.5 | 66.7 | 66.7 | 66.7 |
| Evaluation Results | Difficulty of dirt adhesion | Adhesion ratio (%) of zirconia beads | 1.1 | 14.7 | 7.2 | 21.8 |
| | Feel in dry state | Non-stickiness | 12 | 9 | 10 | 9 |
| | Drying speed | Ratio of water content after rinsing of treated hair bundle, to water content after rinsing of untreated hair (%) | 76 | 9 | 14 | 20 |
| | Feel in dry state after 7-time shampooing | Non-stickiness | 12 | 9 | 9 | 10 |
| | Drying speed after 7-time shampooing | Ratio of water content after rinsing of treated hair bundle, to water content after rinsing of untreated hair (%) | 65 | 23 | 23 | 40 |

TABLE 4

| (mass %) | | | Example 2 | Example 9 | Example 10 |
|---|---|---|---|---|---|
| (A) | (A1-2) Trimethylsiloxysilocate | X-21-5595 *1 | 8.0 | | |
| | (A1-1) Polymethylsilsesquioxane | Silform Flexible Resin *7 | | 8.0 | |
| | (A2-1) (Acrylates/dimethicone) copolymer | KP-550 *8 | | | 8.0 |
| (B) | High-molecular weight dimethylpolysiloxane viscosity 20,000,000 mm²/s | Silsoft B3020 *2 | 4.0 | 4.0 | 4.0 |
| (C) | Isododecane | Marukasol R *3 | Balance | Balance | Balance |
| | Total | | 100 | 100 | 100 |
| | Total content of (A) + (B) (mass %) | | 12.0 | 12.0 | 12.0 |
| | Ratio by mass of content (A) in (A) + (B) (%) | | 66.7 | 66.7 | 66.7 |
| Evaluation Results | Difficulty of dirt adhesion | Adhesion ratio (%) of zirconia beads | 14.7 | 0.7 | 0.3 |
| | Feel in dry state | Non-stickiness | 9 | 12 | 12 |
| | Drying speed | Ratio of water content after rinsing of treated hair bundle, to water content after rinsing of untreated hair (%) | 9 | 40 | 40 |
| | Feel in dry state after 7-time shampooing | Non-stickiness | 9 | 12 | 12 |
| | Drying speed after 7-time shampooing | Ratio of water content after rinsing of treated hair bundle, to water content after rinsing of untreated hair (%) | 23 | 61 | 28 |

TABLE 5

| (mass %) | | | Example 2 | Example 11 |
|---|---|---|---|---|
| (A) | (A1-2) Trimethylsiloxysilocate | X-21-5595 *1 | 8.0 | 8.0 |
| (B) | High-molecular weight dimethylpolysiloxane viscosity 20,000,000 mm²/s | Silsoft B3020 *2 | 4.0 | 4.0 |
| (D) | Red No. 202 | | — | 2.0 |
| (C) | Isododecane | Marukasol R *3 | Balance | Balance |
| | Total | | 100 | 100 |
| | Total content of (A) + (B) (mass %) | | 12.0 | 12.0 |
| | Ratio by mass of content (A) in (A) + (B) (%) | | 66.7 | 66.7 |
| Evaluation Results | Difficulty of dirt adhesion | Adhesion ratio (%) of zirconia beads | 14.7 | 3.6 |
| | Feel in dry state | Non-stickiness | 9 | 9 |
| | Drying speed | Ratio of water content after rinsing of treated hair bundle, to water content after rinsing of untreated hair (%) | 9 | 28 |
| | Feel in dry state after 7-time shampooing | Non-stickiness | 9 | 9 |
| | Drying speed after 7-time shampooing | Ratio of water content after rinsing of treated hair bundle, to water content after rinsing of untreated hair (%) | 23 | 30 |
| | Shampooing Resistance (difficulty of discoloration by shampooing | ΔE* after 7-time shampooing | — | 3.0 |

Ingredients shown in the tables are as described below.

*1: X-21-5595, by Shin-Etsu Chemical Industry Co., Ltd., isododecane solution of trimethylsiloxysilicate (60 mass %)

*2: Silsoft B3020, by Momentive Performance Materials Corporation, high-molecular weight dimethylpolysiloxane, viscosity at 25° C.: 20,000,000 mm²/s

*3: Marukasol R, by Maruzen Petrochemical Co., Ltd., isododecane

*4: X-21-5686, by Shin-Etsu Chemical Industry Co., Ltd., high-molecular-weight dimethylpolysiloxane, viscosity at 25° C.: 3,000,000 mm²/s

*5: X-25-9074, by Shin-Etsu Chemical Industry Co., Ltd., high-molecular-weight dimethylpolysiloxane, viscosity at 25° C.: 30,000,000 mm²/s

*6: KF-96H-1,000,000cs, by Shin-Etsu Chemical Industry Co., Ltd., high-molecular-weight dimethylpolysiloxane, viscosity at 25° C.: 1,000,000 mm²/s

*7: SilForm Flexible Resin, by Momentive Performance Materials Corporation, polymethylsilsesquioxane

*8: KP-550, by Shin-Etsu Chemical Industry Co., Ltd., isododecane solution of (acrylates/dimethicone) copolymer (40 mass %)

The degree of polymerization (P) of the components *2, and 4 to 6 can be calculated as follows. From the viscosity (q), the molecular weight (M) is derived according to the above-mentioned formula (4). Since the molecular weight of the base unit of dimethylpolysiloxane is 74, the degree of polymerization (P) is calculated according to the following formula (5).

$$P=M/74 \qquad (5)$$

From Tables 1 to 5, it is known that, by applying the cosmetic composition of the present invention to hair, a dirt adhesion preventing effect, a good feel and a high drying speed can be given, and even after washing, these effects can be sustained well.

INDUSTRIAL APPLICABILITY

According to the present invention, there can be provided a cosmetic composition which, when applied to keratin substances such as skin or hair, can impart thereto a dirt adhesion preventing effect, a good feel and a high drying speed, and even after shampooing, these effects can be sustained. In addition, when the cosmetic composition is used as a hair dye composition, it can impart the above-mentioned effects to hair and secures good color duration with little discoloration by shampooing.

The invention claimed is:

1. A cosmetic composition comprising:
   (A) a silicone film-forming agent, and
   (B) a high-molecular-weight organopolysiloxane having a degree of polymerization of 2,600 or more and 4,500 or less, wherein:
   a ratio by mass of a content of the component (A) to a total content of the component (A) and the component (B), [(A)/((A)+(B))] is 50% or more and 98% or less, and a water content is 10% by mass or less.

2. The cosmetic composition according to claim 1, wherein the component (A) is at least one selected from the group consisting of the following components (A1) and (A2):
   (A1) a silicone resin represented by an average formula, $(R^1)_m SiO_{(4-m)/2}$
   wherein $R^1$ represents a hydrocarbon group having 1 or more and 12 or less carbon atoms and optionally substituted with fluorine, or a hydroxy group, plural $R^1$'s can be the same as or different from each other, and m is an average number, representing a number of more than 0 and less than 3,
   which contains at least one unit selected from the group consisting of a T unit represented by $R^1 SiO_{3/2}$ and a Q unit represented by $SiO_{4/2}$,
   (A2) a silicone polymer containing a polysiloxane moiety and a moiety formed of a non-silicone organic chain.

3. The cosmetic composition according to claim 2, wherein the component (A2) contains an acryl silicone polymer (A2-1).

4. The cosmetic composition according to claim 1, wherein the component (B) is an organopolysiloxane represented by the following general formula (1):

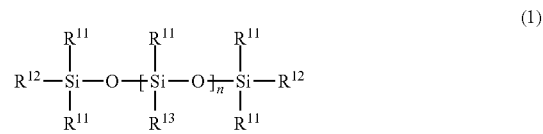

wherein $R^{11}$ each independently represents a hydrocarbon group having 1 or more and 6 or less carbon atoms, $R^{12}$ each independently represents a hydroxy group, an alkoxy group having 1 or more and 6 or less carbon atoms, or a hydrocarbon group having 1 or more and 6 or less carbon atoms, $R^{13}$ represents a hydrocarbon group having 1 or more and 6 or less carbon atoms, or a primary to tertiary amino group-containing group, n indicates a degree of polymerization, and is a number of 2,600 or more and 4,500 or less, and n's $R^{13}$'s can be the same as or different from each other.

5. The cosmetic composition according to claim 1, wherein a total content of the component (A) and the component (B) in the cosmetic composition is 1% by mass or more and 50% by mass or less.

6. The cosmetic composition according to claim 1, further containing a solvent as a component (C) in an amount of 40% by mass or more.

7. The cosmetic composition according to claim 1, further containing a functional powder as a component (D).

8. The cosmetic composition according to claim 1, which is a hair cosmetic composition.

9. The cosmetic composition according to claim 1, which is a hair dye composition.

10. A method for treating a keratin substance, comprising applying the cosmetic composition of claim 1 to the keratin substance and then drying it.

11. A method for treating hair, comprising applying the hair cosmetic composition of claim 8 to the hair and then drying it.

12. A method for dyeing hair, comprising applying the hair dye composition of claim 9 to the hair and then drying it.

13. A cosmetic kit, comprising compositions (I) and (II),
   (I) a composition containing (A) a silicone film-forming agent,
   (II) a composition containing (B) a high-molecular-weight organopolysiloxane having a degree of polymerization of 2,600 or more and 4,500 or less.

* * * * *